US008380289B2

(12) United States Patent
Zellers et al.

(10) Patent No.: US 8,380,289 B2
(45) Date of Patent: Feb. 19, 2013

(54) MEDICAL DEVICE LOCATION SYSTEMS, DEVICES AND METHODS

(76) Inventors: Robert D. Zellers, Lafayette, CO (US); Peter E. Nelson, Longmont, CO (US); Charles W. Henry, Denver, CO (US)

( * ) Notice: Subject to any disclaimer, the term of this patent is extended or adjusted under 35 U.S.C. 154(b) by 272 days.

(21) Appl. No.: 12/949,671

(22) Filed: Nov. 18, 2010

(65) Prior Publication Data

US 2012/0130229 A1     May 24, 2012

(51) Int. Cl.
    *A61B 5/05*     (2006.01)
(52) U.S. Cl. ........ 600/426; 600/407; 600/410; 600/424; 600/448
(58) Field of Classification Search .................. 600/407, 600/410, 424, 426, 448
See application file for complete search history.

(56) References Cited

U.S. PATENT DOCUMENTS

| | | |
|---|---|---|
| 4,173,228 A | 11/1979 | Van Steenwyk et al. |
| 4,560,930 A | 12/1985 | Kouno |
| 5,005,592 A | 4/1991 | Cartmell |
| 5,099,845 A | 3/1992 | Besz et al. |
| 5,307,072 A | 4/1994 | Jones |
| 5,429,132 A | 7/1995 | Guy et al. |
| 5,558,091 A | 9/1996 | Acker et al. |
| 5,645,065 A | 7/1997 | Shapiro et al. |
| 5,729,129 A | 3/1998 | Acker |
| 5,879,297 A | 3/1999 | Haynor et al. |
| 5,913,820 A | 6/1999 | Bladen et al. |
| 6,487,516 B1 | 11/2002 | Amorai-Moriya |
| 6,516,212 B1 | 2/2003 | Bladen et al. |
| 6,522,907 B1 | 2/2003 | Bladen et al. |
| 6,615,155 B2 | 9/2003 | Gilboa |
| 6,690,963 B2 | 2/2004 | Ben-Haim et al. |
| 6,701,179 B1 | 3/2004 | Martinelli et al. |
| 6,757,557 B1 | 6/2004 | Bladen et al. |
| 6,774,624 B2 | 8/2004 | Anderson et al. |
| 7,174,202 B2 | 2/2007 | Bladen et al. |
| 7,366,562 B2 | 4/2008 | Dukesherer et al. |

OTHER PUBLICATIONS

Solomon, S. et al., "TIPS placement in swine, guided by electromagnetic real-time needle tip localization displayed on previously acquired 3-D CT," Cardiovascular and Interventional Radiology; vol. 22, No. 5; pp. 411-414; Sep. 1999.

Schneider, M., "Electromagnetic Tracking for Catheter Localization," Part of the SPIE Conference on Biomedical Diagnostic, Guidance, and Surgical-Assist Systems; San Jose, California; SPIE; vol. 3595; pp. 61-68; Jan. 1999.

*Primary Examiner* — Brian Casler
*Assistant Examiner* — Joel Lamprecht
(74) *Attorney, Agent, or Firm* — Berenbaum Weinshienk PC

(57) ABSTRACT

Methods, devices and systems for one or both of two- or three-dimensional location of the disposition of a sensor coil in a subject including: an array of electromagnetic drive coil sets, each set having two or three dimensionally oriented drive coils; a sensor coil being electromagnetically communicative with the array of electromagnetic drive coil sets; and, a system controller communicative with and adapted to energize one or more of the electromagnetic coils in the array of electromagnetic drive coil sets, the energizing of the one or more of the electromagnetic coils including one or more of energizing the coils singly, or in pairs of x-y and y-z or x-z coils, or in triplets of x-y-z coils while measuring the response of the sensor coil; whereby the system uses the measurements of the responses of the sensor coil to calculate the location and orientation of the sensor coil relative to said drive coil sets.

33 Claims, 20 Drawing Sheets

MEDICAL DEVICE LOCATION SYSTEMS, DEVICES AND METHODS

BACKGROUND

In medical care, the correct placement of a medical device such as a catheter or a guide wire in a patient has become increasingly important for a number of reasons. In the case of an infusion catheter, for example, medications can need to be targeted to, or for, specific organs, or areas of the body. A catheter can need to be located sufficiently near the heart in a particular region where there is a particular blood flow rate; as for example, a particular high blood flow rate to ensure adequate dilution/mixing of infused fluids. Alternatively, a catheter or other internally-positioned medical device can simply need to be disposed in the right place to function; as for example, an enteral feeding tube within the stomach. Use of a medical device position location and/or guidance system can thus provide for less skilled practitioners to accurately and reliably position a medical device such as a catheter.

Accordingly, a variety of systems have been developed to attempt to indicate location or position of catheters within the body of a patient. Relatively reliable location devices have made use of x-ray or fluoroscopy; however, these devices expose the patient and/or caregiver to undesirable amounts of radiation. As a consequence, a variety of different systems have been attempted to more continuously and accurately indicate location of a catheter with a goal of replacing the use of x-rays. However, such systems still suffer from various problems.

Electromagnetic catheter position location devices have been in development. Some position location systems have made use of alternating current, AC, driven external coils with a sensor (sensor coil) in the catheter tip. Others have used an AC driven coil in the catheter tip with external sensor coils. A disadvantage of such a conventional catheter tip driven system has been the need for heavy or thick wires running into the catheter to carry sufficient drive current to generate a sufficient electromagnetic signal for the external sensors. This has precluded the use of such a system with smaller diameter catheters. Other position location systems have used a fixed (or DC) magnet on the catheter tip with external sensor coils. A significant disadvantage to such a fixed magnet location system has been that the magnet would necessarily be very small, and as such would generate a very small signal from the tip of the catheter. As a consequence, other magnetic fields in the vicinity can create significant interference problems for such a system. Furthermore, the field of such a magnet drops off extremely quickly over distance and thus cannot be sensed more than a few inches deep into the patient's tissue. Another AC drive system has been described including driving two coils simultaneously; however, those respective coils were specified as having been driven at two different frequencies so that the coil drives are not additive and the sensor demodulates the two different frequencies as two independent values. Yet another AC drive system has been described driving two coils simultaneously in quadrature which simulates a single spinning coil; however, this system can only indicate the orientation of the sensor in the x-y plane and its relative position in that plane.

This statement of background is for information purposes only and is not intended to be a complete or exhaustive explication of all potentially relevant background art.

SUMMARY

Devices, methods and systems of the present developments can include a sensor coil that may be associated with a medical device such as a catheter, this sensor coil being communicatively cooperative with, or responsive to an array of drive coil sets of drive coils placed relative to a subject's body to allow detection or positioning of the medical device in the subject's body. Each of the drive coil sets and the sensor coil may also be communicatively connected or cooperative with an external control and/or display box, for selective driving of the drive coils of the sets of drive coils and for receiving response signals from the sensor coil.

Methods, devices and systems can be provided can be provided for one or both of two- or three-dimensional location of the disposition of a sensor coil in a subject including: an array of electromagnetic drive coil sets, each set having two or three dimensionally oriented drive coils; a sensor coil being electromagnetically communicative with the array of electromagnetic drive coil sets; and, a system controller communicative with and adapted to energize one or more of the electromagnetic coils in the array of electromagnetic drive coil sets, the energizing of the one or more of the electromagnetic coils including one or more of energizing the coils singly, or in pairs of x-y and y-z or x-z coils while measuring the response of the sensor coil; whereby the system uses the measurements of the responses of the sensor coil to calculate the location and orientation of the sensor coil relative to said drive coil sets.

These and still further aspects and advantages of the present developments are illustrative of those which can be achieved by these developments and are not intended to be exhaustive or limiting of the possible advantages which can be realized. Thus, these and other aspects and advantages of these present developments will be apparent from the description herein or can be learned from practicing the disclosure hereof, both as embodied herein or as modified in view of any variations which can be apparent to those skilled in the art. Thus, in addition to the exemplary aspects and embodiments described above, further aspects and embodiments will become apparent by reference to and by study of the following descriptions, including as will be readily discerned from the following detailed description of exemplary implementations hereof especially when read in conjunction with the accompanying drawings in which like parts bear like numerals throughout the several views.

DETAILED DESCRIPTION OF FIGURES

Figure 1:
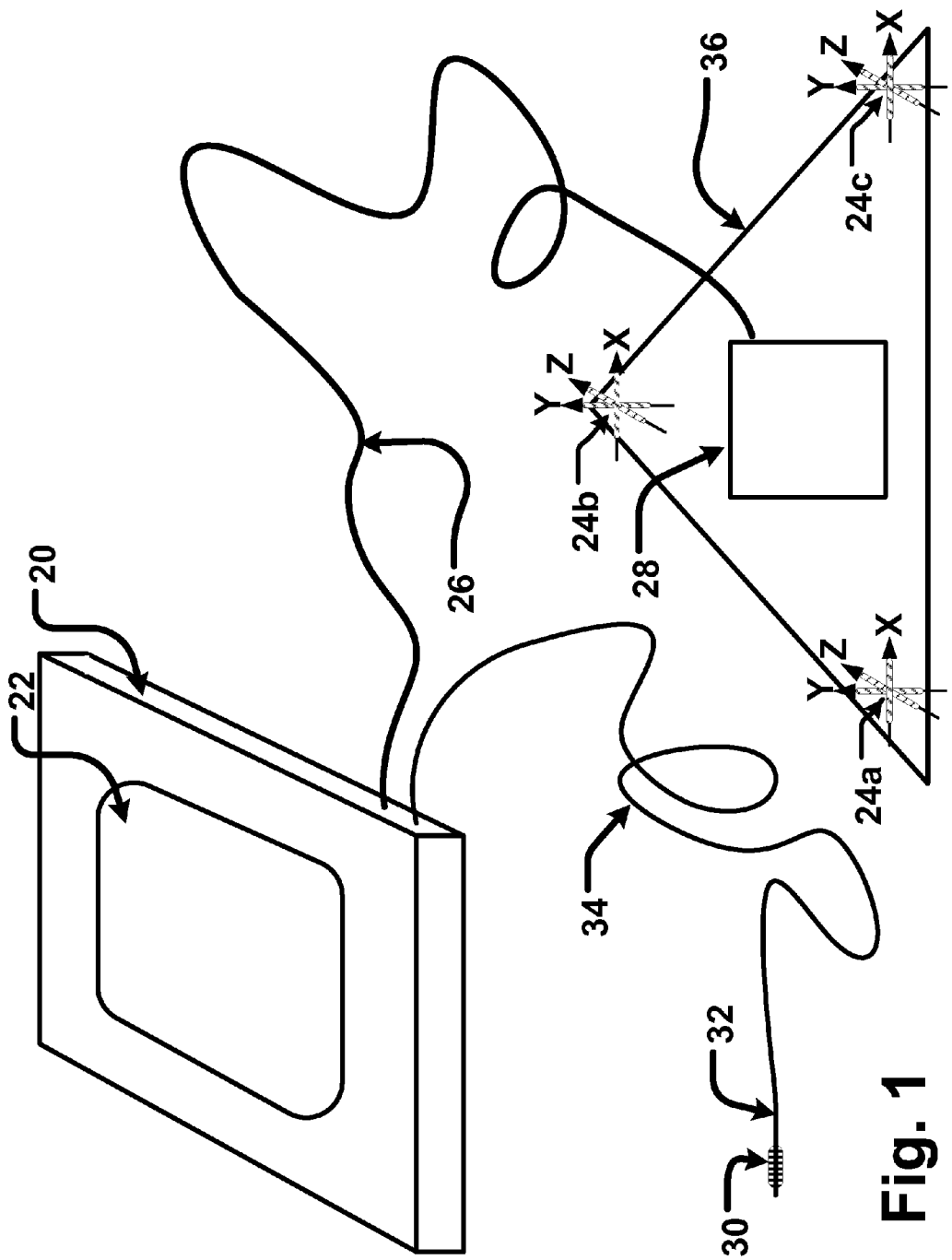
FIG. 1 is a schematic overview of present developments showing a user control box, and a patient drive coil block with drive coil sets, and a guide wire or stylet with a sensor coil and cable.

FIG. 1 provides an overview of an implementation of a medical device location system hereof. A user control box 20 may be included, and according to this implementation, contains a touch screen display 22, a single-board computer (SBC) (not separately shown in FIG. 1) for control and data processing, and a main interface board (also not separately shown in FIG. 1) which connects to a drive block cable 26 and a medical device cable 32 (also sometimes referred to as a catheter, or guide wire or stylet cable 32). A triangular patient drive coil block 36 may be connected via drive block cable 26 to the control box 20 (the drive coil block also sometimes being referred to as an emitter block, a patient block or merely a drive block). Coil drive electronics 28 and three drive coil sets 24a, 24b, 24c (also sometimes referred to as emitter coils, or x-y-z drive coils) are mounted in the drive block 36. The coil drive electronics 28 allow the SBC to selectively energize any drive coil axis 38, 40, 42 of a set 24 (see FIG. 2) or group of drive coil axes. A sensor coil 30 is, in this implementation, built on or within the tip of a medical device such as a small diameter biocompatible guide wire or stylet cable 32. The guide wire may then be placed in the patient and the catheter then threaded over this wire; or, alternatively, the stylet cable may then be inserted up to the distal end of a catheter before the catheter is placed in the patient. A two-conductor cable 34 can be used to connect the sensor coil of guide wire or stylet back to the user control box.

Figure 2:
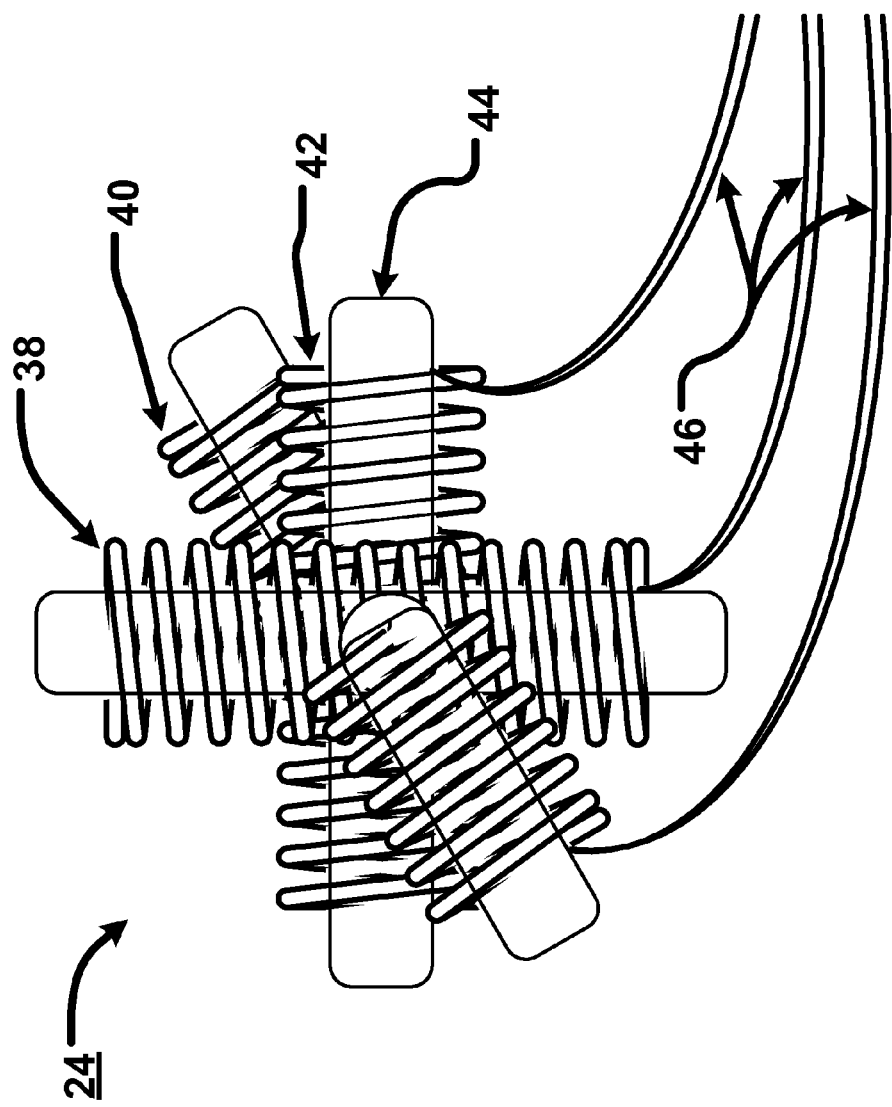
FIG. 2 is a detailed view of one three-axis drive coil set.

FIG. 2 shows a detailed drawing of a drive coil set 24 (representative of any of sets 24a, 24b, 24c). Here, the x-coil 42, the y-coil 38 and z-coil 40 each have a ferrite or ferrous core 44 to enhance the magnetic field generation. This figure is only schematically representative of the construction of a drive coil; in actuality, each drive coil may have many windings (e.g. 100 turns) on the ferrite core and can be constructed as three (3) coil pairs to facilitate the intersection of the x, y, and z axes. Each coil here has a set of lead wires 46 to connect back to the multiplexers of the coil drive electronics 28.

Figure 3:
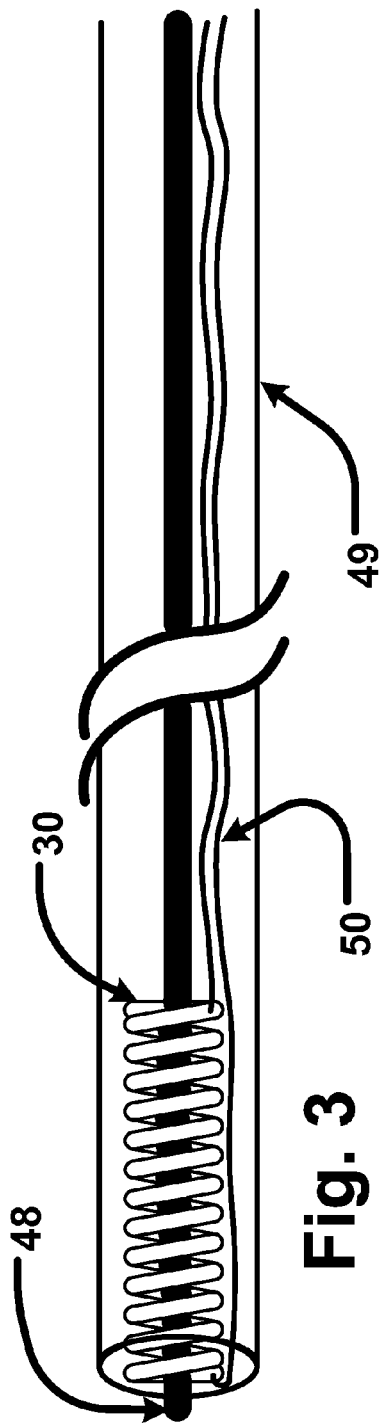
FIG. 3 is a detailed view of a sensor coil.

FIG. 3 shows a detailed view of an exemplar medical device; e.g., a guide wire or stylet sensor coil. The sensor coil 30 can be any suitable gauge (e.g., but not limited to, a very fine gauge (e.g. 0.001" diameter)) insulated wire wound around a ferrous core wire 48. This figure is schematically illustrative only of the sensor coil; here, the sensor coil is approximately 400 turns in single layer, but can be any suitable turns per length, e.g., 50-1000, or any range or value therein, e.g., 100, 200, 300, 350, 400, 450, 500, 550, 600, 650, 700, and the like. An alternative construction can optionally be 400 or more turns in 2, 3, 4, 5, or more layers; here, the advantage of multiple even layers may be the lead wires come off the same end of the coil. The sensor coil lead wires 50 connect back through a cable to the patient isolated portion of the main interface board. A thin insulating tubing 49 can be used to provide a protective sleeve for the whole assembly.

In an optional ECG version of a catheter location system (e.g., FIG. 7), the tip of the ferrous, conductive core wire 48 can be polished smooth and can provide an electrical signal as an ECG lead from within the catheter. In such a version, the guide wire or stylet sensor connection is accomplished with three wires, two (2) for the coil sensor and one (1) for the ECG, through a cable 54 to the patient isolated portion of the main interface board in the user control box 20. Furthermore, the patient drive coil block 60 can have two ECG pads added which connect through a cable 62 to the patient isolated portion of the main interface board. These two ECG inputs together with the one ECG from the catheter provide a three-lead ECG measurement system (e.g., see FIG. 10).

Figures 5, 6:
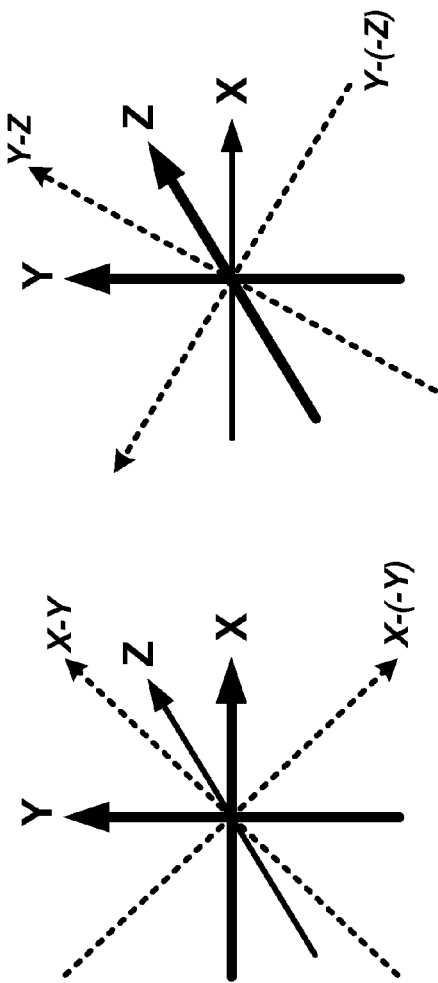
FIG. 5 is an illustration of orthogonal magnetic vectors generated by an x-y virtual drive.
FIG. 6 is an illustration of orthogonal magnetic vectors generated by a y-z virtual drive.
Figure 4:
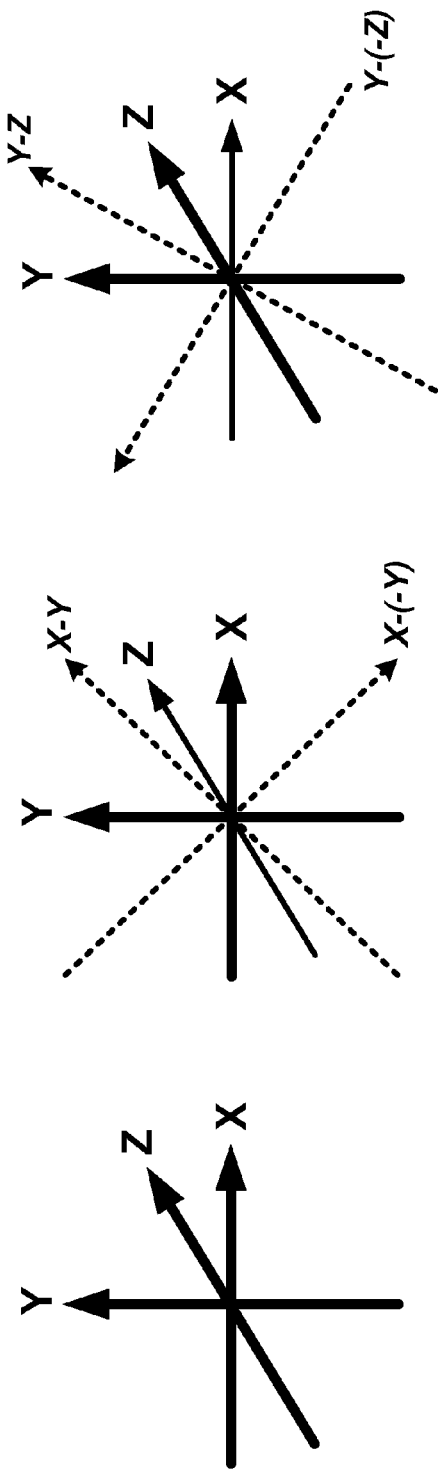
FIG. 4 is an illustration of magnetic vectors generated by a normal coil drive.

FIGS. 4, 5 and 6 illustrate an optional version of the operation of a normal-drive and virtual-drive drive coil set. FIG. 4 shows magnetic vectors x, y, and z generated by normal coil driving of the x-axis coil 42, the y-axis coil 38 and z-axis coil 40 (as shown in FIG. 2). FIG. 5 shows the virtual magnetic vector x-y generated by simultaneously driving the x-axis coil 42 and the y-axis coil 38 (as shown in FIG. 2) and when both are driven at the same power, the vector is forty-five degrees between the x and y axes. The virtual magnetic vector x-(-y) generated by simultaneously driving the x-axis coil 42 and the phase-inverted, y-axis coil 38 (as shown in FIG. 2) and when both are driven at the same power, the vector is minus forty-five degrees between the x and -y axes. If a digital to analog converter (DAC) is added to control power to the x-axis drive and another DAC added to control power of y-axis drive, then it is possible to point the virtual axis to any angle from 0 to 360 degrees between x and y. For example, if x-axis power DAC is maximum and y-axis power DAC is $\frac{1}{4}^{th}$ (one quarter) of maximum then the vector sum of x-y drive yields a virtual axis of approximately fourteen degrees between the x and y axes. FIG. 6 shows a virtual magnetic vector y-z generated by simultaneously driving the z-axis coil 42 and the y-axis coil 38 (as shown in FIG. 2); and a virtual magnetic vector z-(-y) generated by simultaneously driving the z-axis coil 42 and a phase-inverted, y-axis coil 38 (as shown in FIG. 2). These figures illustrate the simplest and one optional form of virtual drive (e.g., see FIG. 13), it is possible to point a virtual magnet vector to any polar coordinate by simultaneously driving x, y, and z coils at independent power levels (e.g., see FIG. 15).

Figure 7:
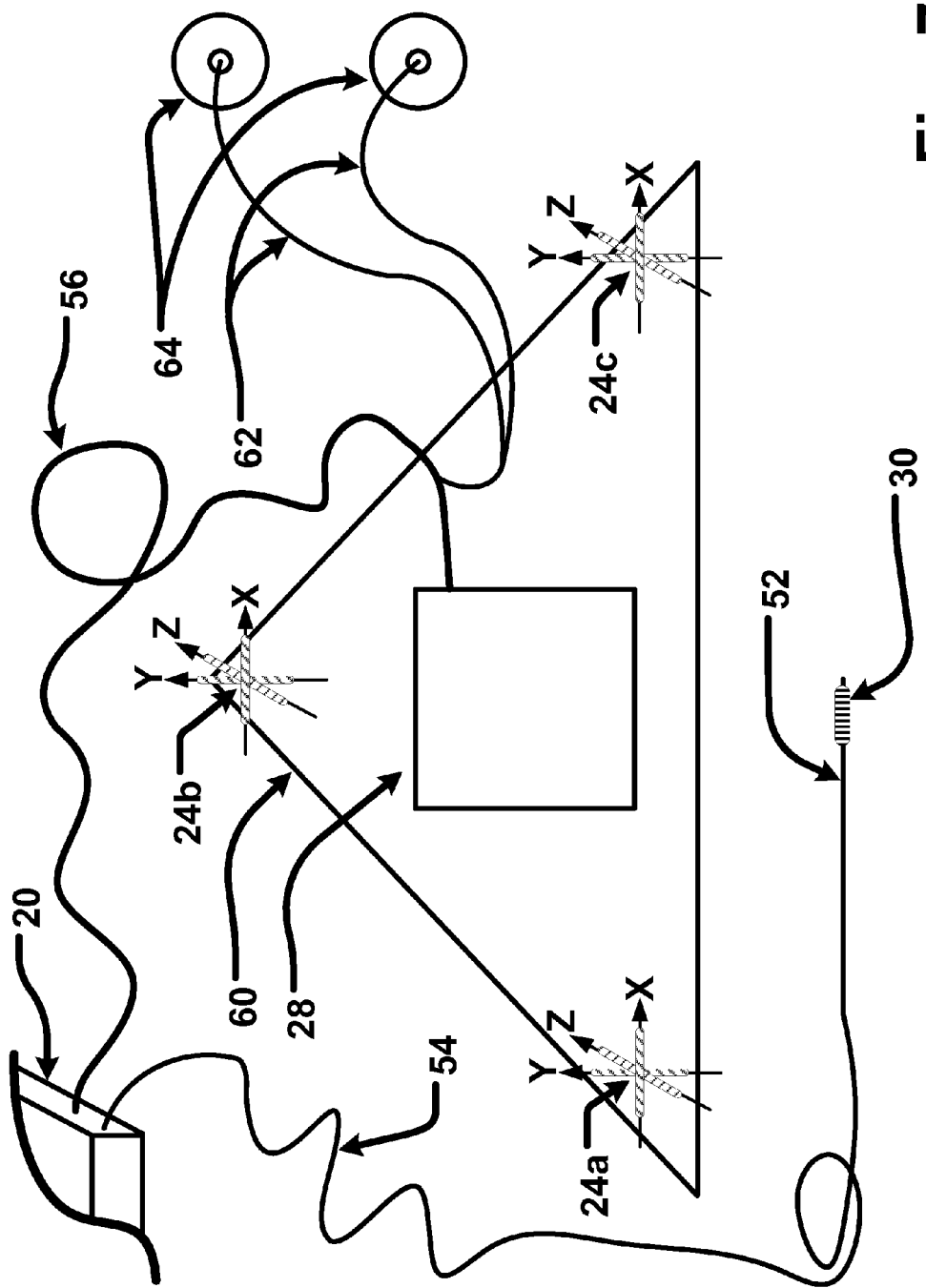
FIG. 7 is a detailed view of a drive coil and sensor coil block with an addition of an optional ECG measurement.

FIG. 7 provides a schematic diagram of an optional medical device location system with optional electrocardiograph (ECG) measurement. This is similar to the FIG. 1 implementation with the addition of three ECG leads. The user control box 20 connects through a main interface board to the drive block cable 56 and guide wire or stylet cable 54. The patient drive block 60 may be connected via drive block cable 56 which includes two isolated ECG lead signals to the control box 20. The coil drive electronics 28 and three x-y-z drive coils 24a, 24b, 24c may be mounted in the drive block 60. The coil drive electronics 28 allow the single board controller (SBC) to selectively energize any drive coil axis 38, 40, 42 (FIG. 2) or group of drive coil axes. Two ECG pads 64 are placed on the patient and connected by ECG lead wires 62 to the drive block 60. The guide wire or stylet sensor 30 here is built onto a small diameter biocompatible conductive-tip guide wire or stylet cable 52 which is inserted into a catheter before (stylet) or after (guide wire) the catheter is placed in the patient. A three-conductor cable 54 connects the guide wire or stylet sensor coil and one ECG lead back to the user control box 20.

Figure 8:
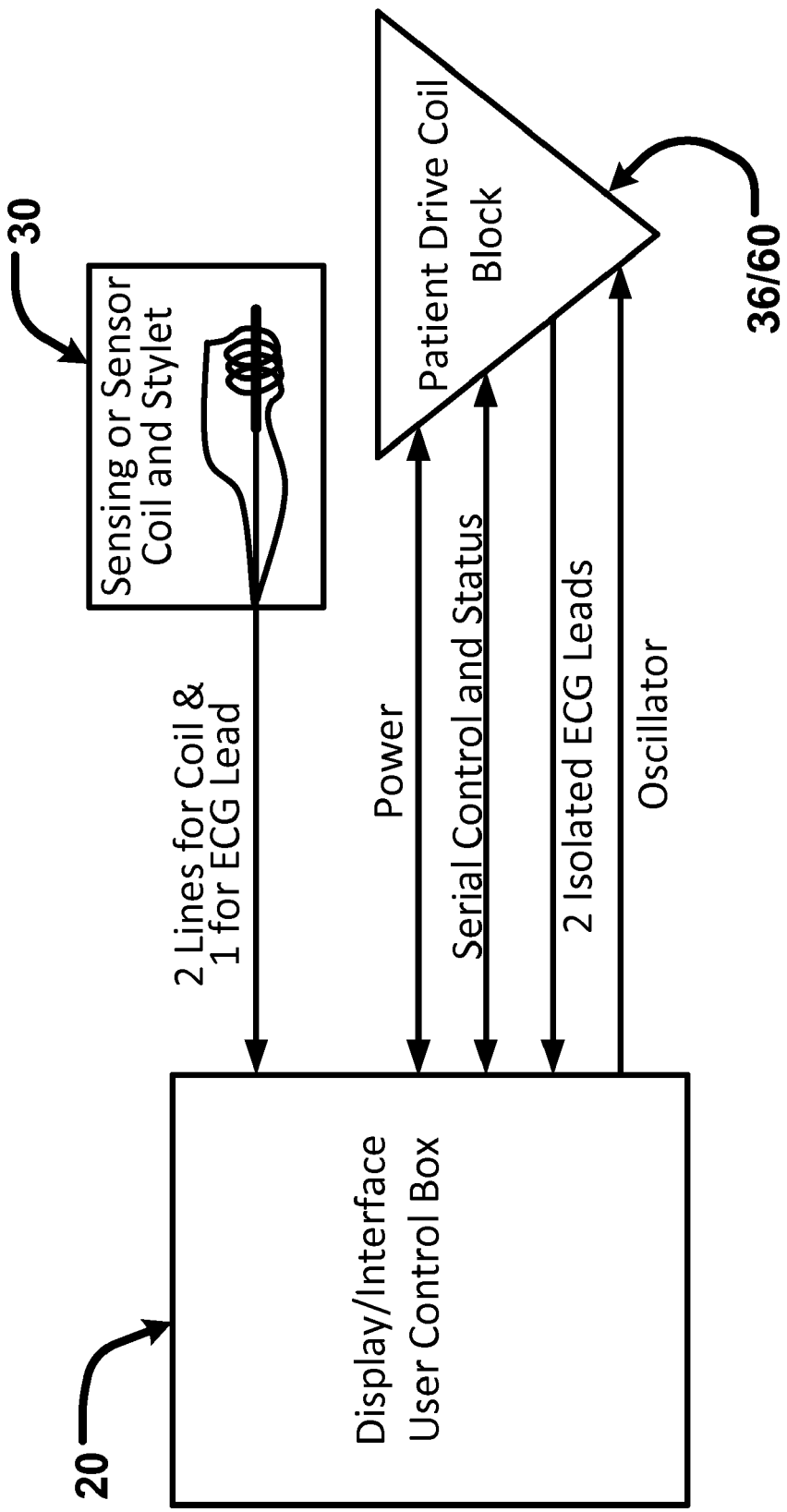
FIG. 8 is a block diagram of a present development hereof.

FIG. 8 is an overall schematic diagram of a medical device location system. This figure illustrates connections between a user control box 20 and a sensing guide wire or stylet 30 and a patient drive block 36, 60. The control box 20 can include an integrated, separated, or remote user display and/or interface. Each of these components can include cables or connectors for one or more of a coil interface, a power supply, a serial interface, a control interface, a status interface, an ECG interface or lead, an oscillator interface, a processor interface, a computer interface, a data interface, a network interface (cable or wireless), an internet interface, a video interface, a touch-screen interface, an SBC control or power interface, a board interface, a sensor interface, an isolator interface, and/or the like as described herein or as known in the art. One or more of these cables or connectors can attach to the patient drive block 36/60 or any component thereof.

Figure 9:
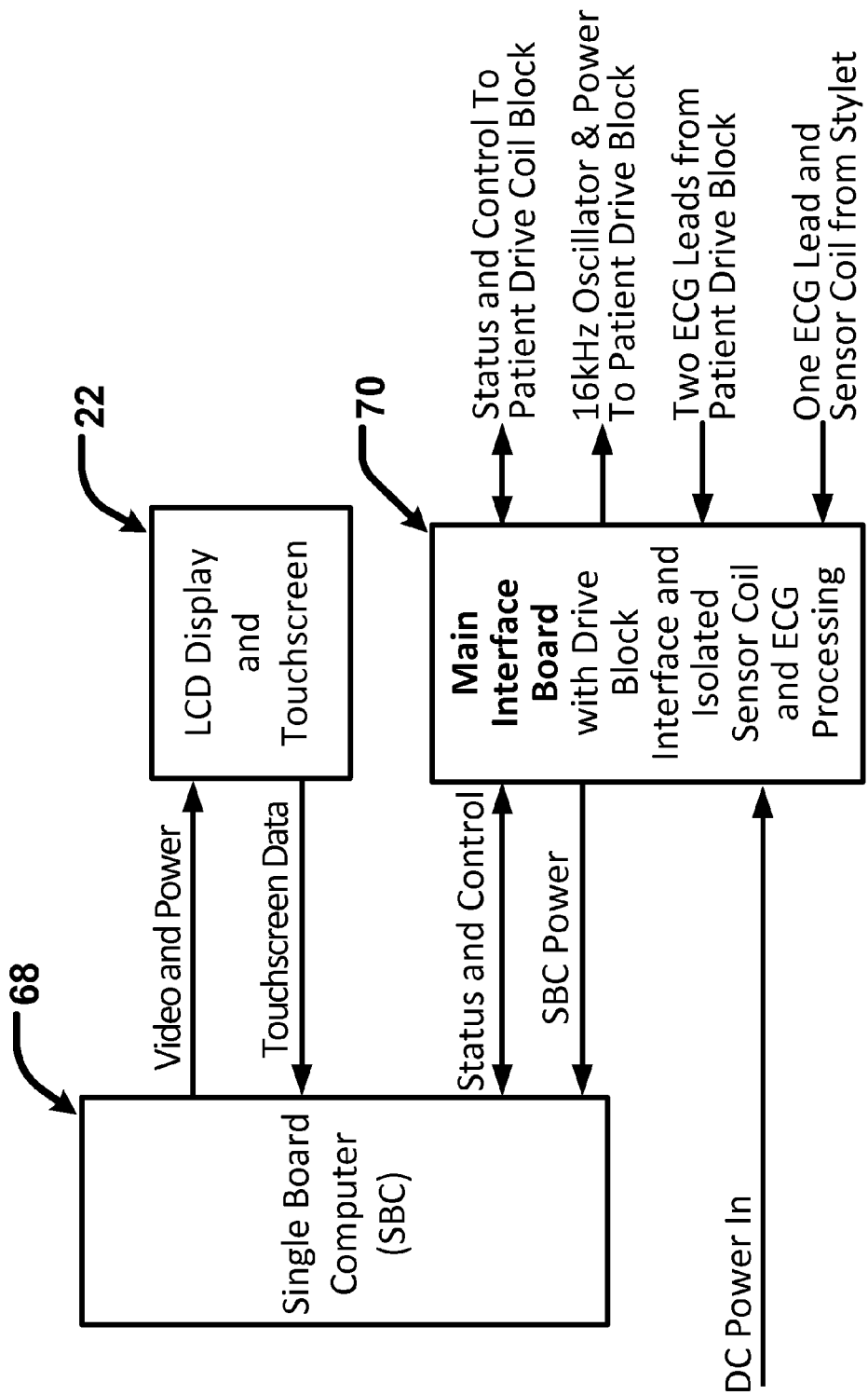
FIG. 9 is a block diagram of a display/interface and user control box.

FIG. 9 is a block diagram of a user control box 20 which in this implementation includes a computer 68, an LCD display 22 with touch-screen, and a main interface board 70. Each of these components can include cables or connectors for one or more of a coil interface, a power supply, a serial interface, a control interface, a status interface, an ECG interface or lead, an oscillator interface, a processor interface, a computer interface, a data interface, a network interface (cable or wireless), an internet interface, a video interface, a touch-screen interface, an computer control or power interface, a board interface, a sensor interface, an isolator interface, and/or the like as described herein or as known in the art.

Figure 10:
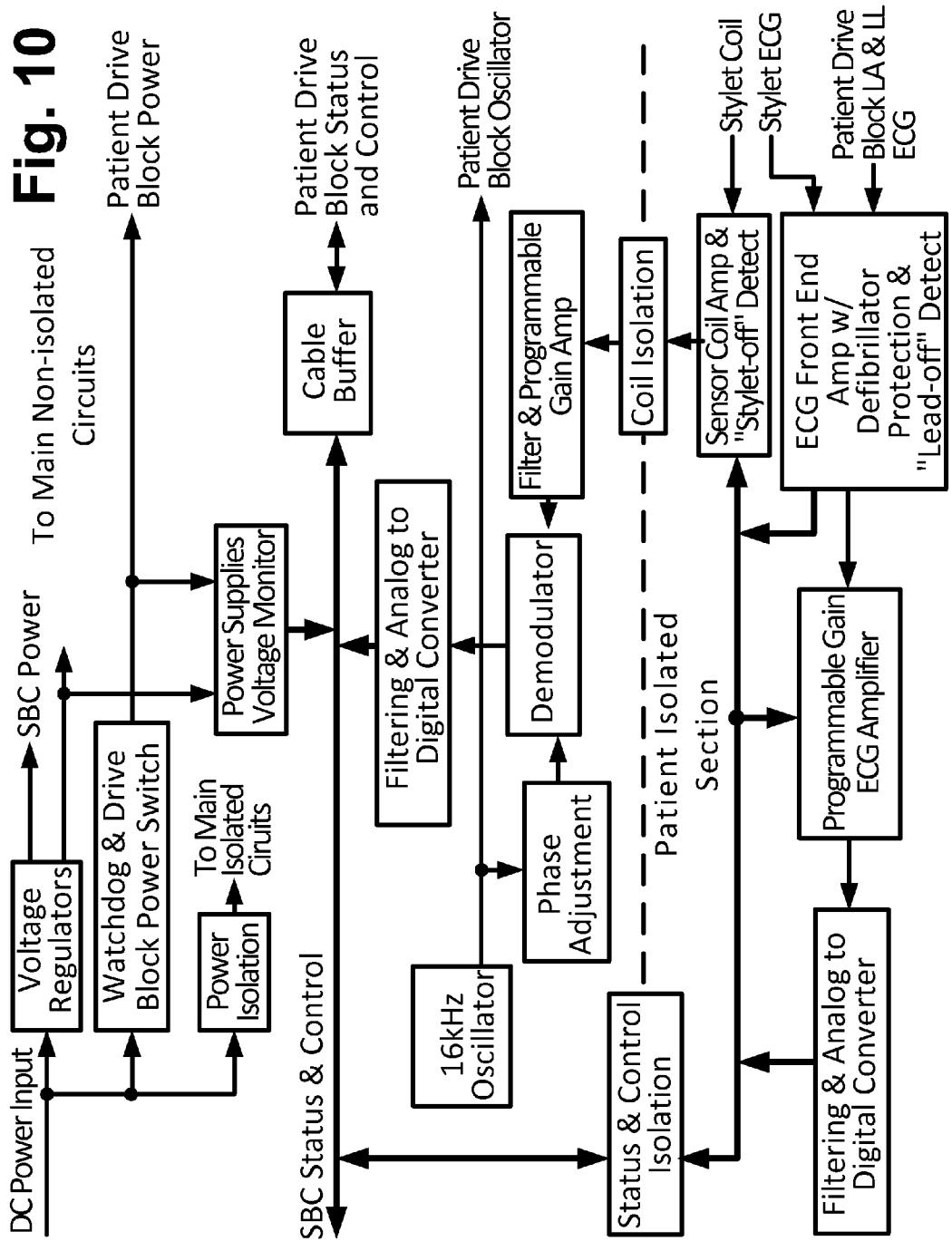
FIG. 10 is a block diagram of a function of a main interface board in a user control box.

FIG. 10 provides a detailed block diagram of a main interface board 70 (FIG. 9) and shows a patient isolated section which connects to a guide wire or stylet cable 34, 54 and an ECG leads from a patient drive block 60. The remainder of the circuitry controls power/interface to a patient drive block 36, 60 and power to a single board computer 68, including one or more of a voltage regulator, a watchdog switch, a drive switch, a power isolator, a voltage monitor, a cable buffer, a filter, an analog to digital converter, a phase adjuster, a demodulator, a signal filter, a programmable gain amplifier, a coil isolator, a coil sensor coil amplifier, a detector, memory, flash memory, a multiplexor, a polarity inversion switch, and/or the like. Each of these components can include cables or connectors for one or more of a coil interface, a power supply, a serial interface, a control interface, a status interface, an ECG interface or lead, an oscillator interface, a processor interface, a computer interface, a data interface, a network interface (cable or wireless), an internet interface, a video interface, a touch-screen interface, an SBC control or power interface, a board interface, a sensor interface, and/or the like as described herein or as known in the art. One or more of these cables or connectors can attach to a patient drive block 36/60 or any component thereof.

Figure 11:
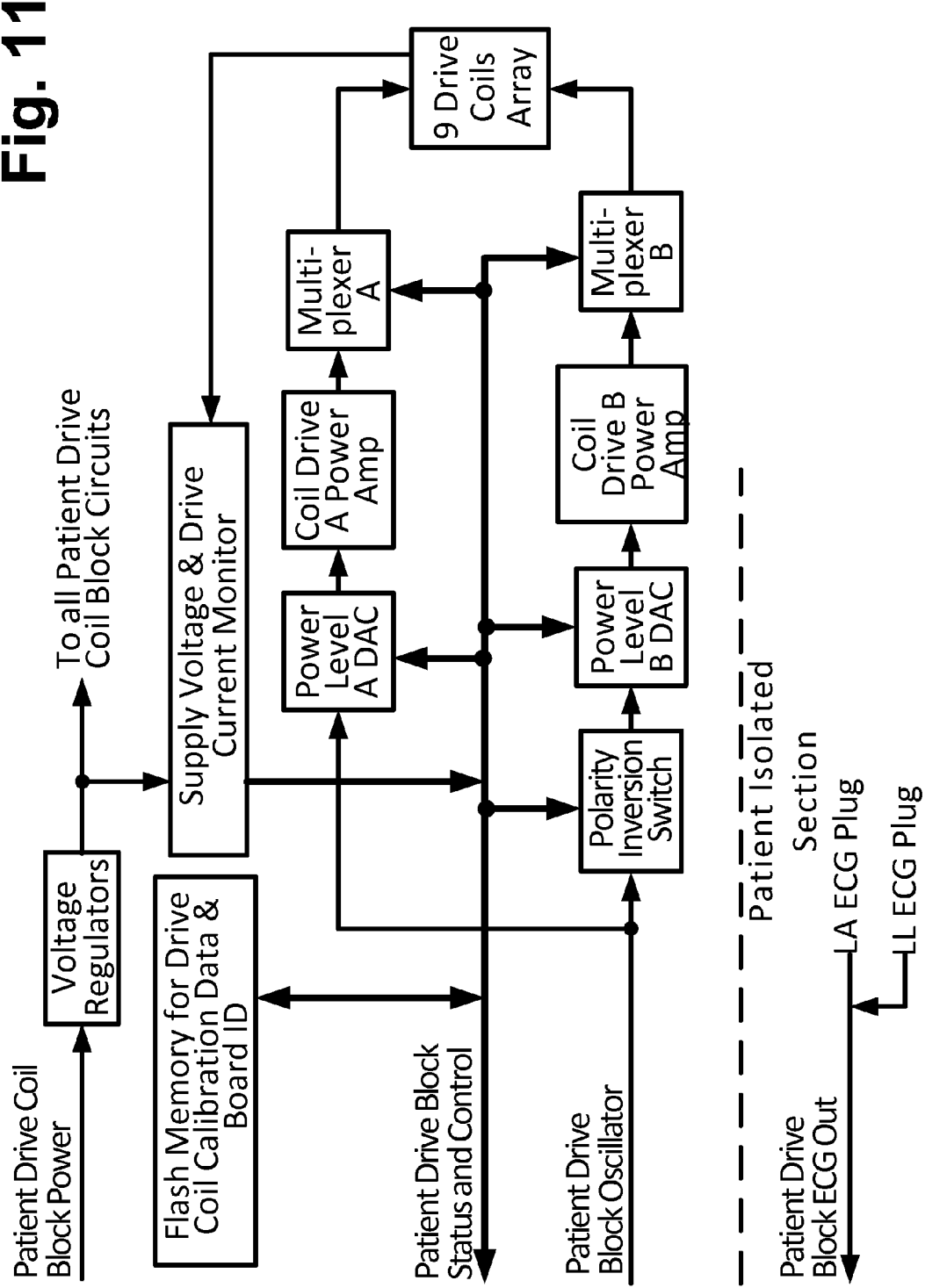
FIG. 11 is a block diagram of an overall function of a patient drive coil block.
Figure 12A:
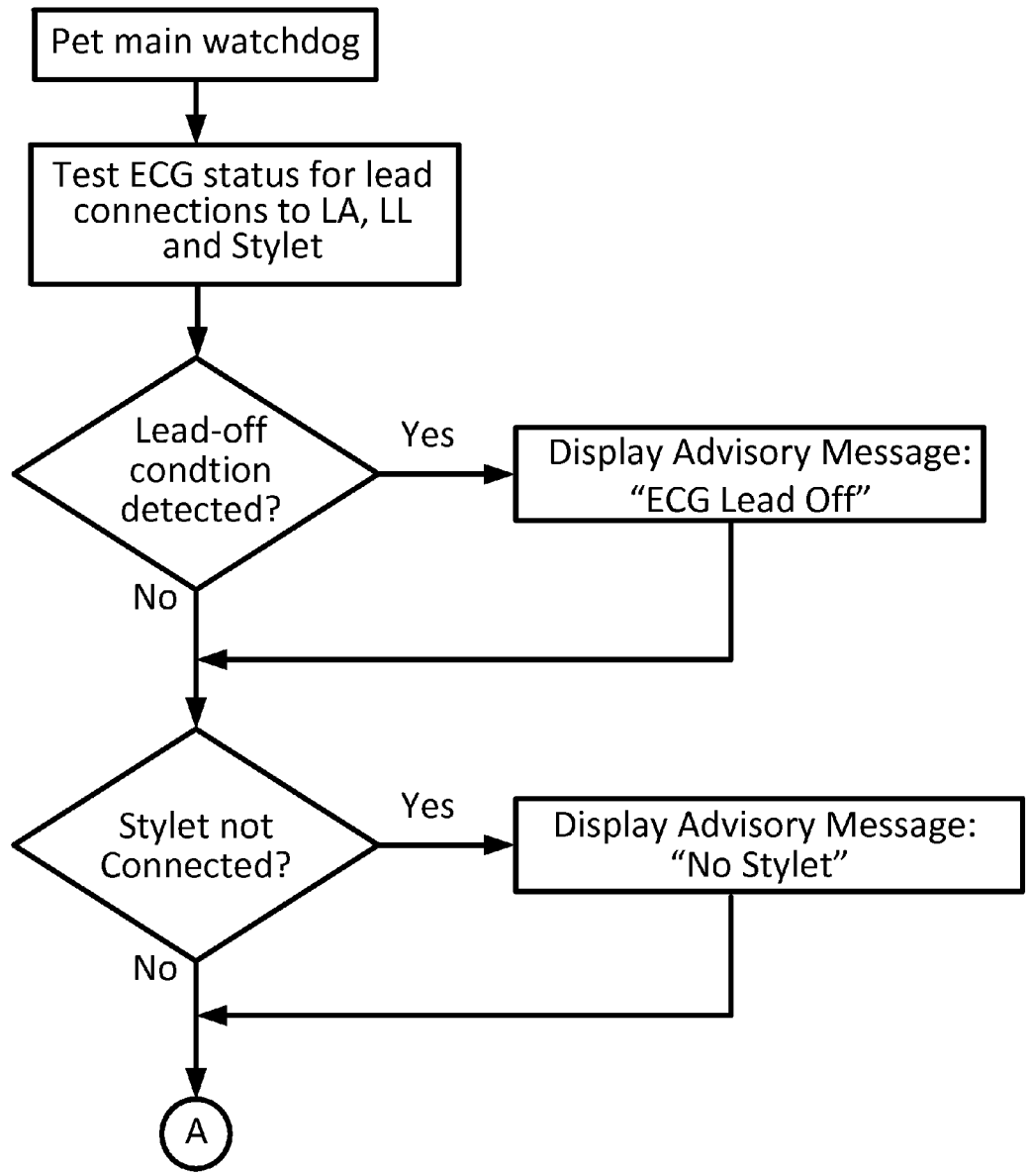
FIG. 12a-12f detail algorithms for controlling an acquisition of sensor coil position optionally including display and/or ECG.
Figure 12B:
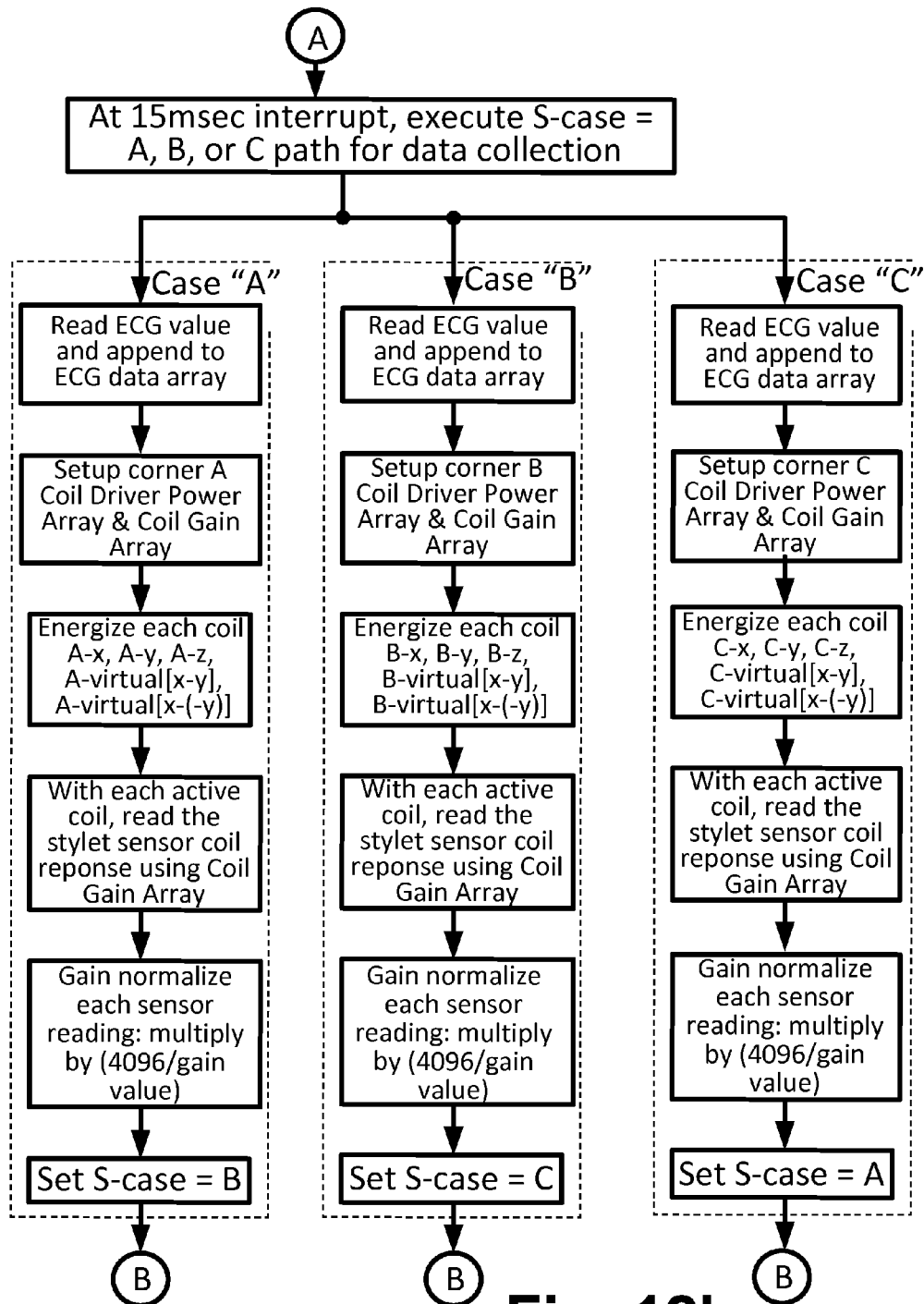
Figure 12C:
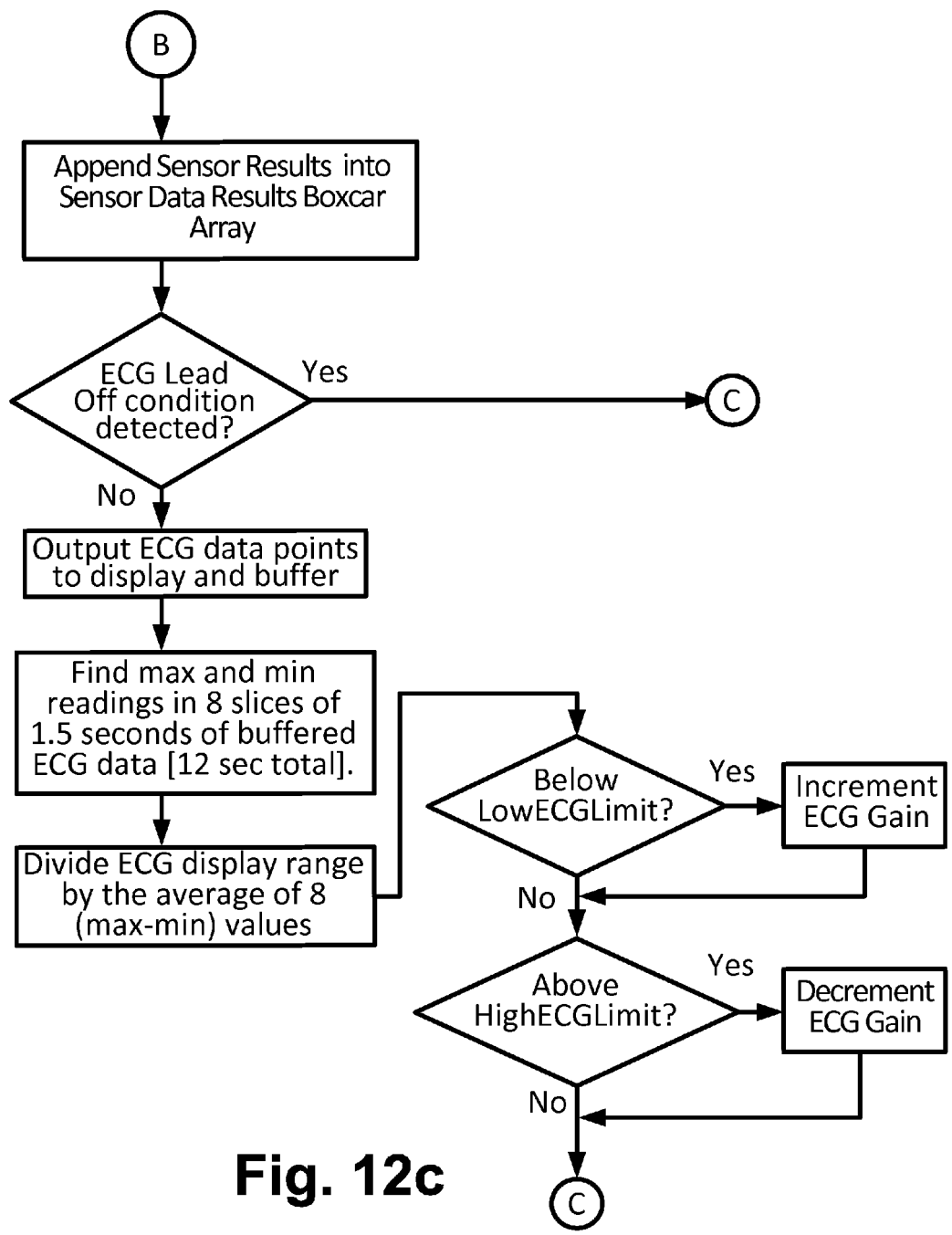
Figure 12D:
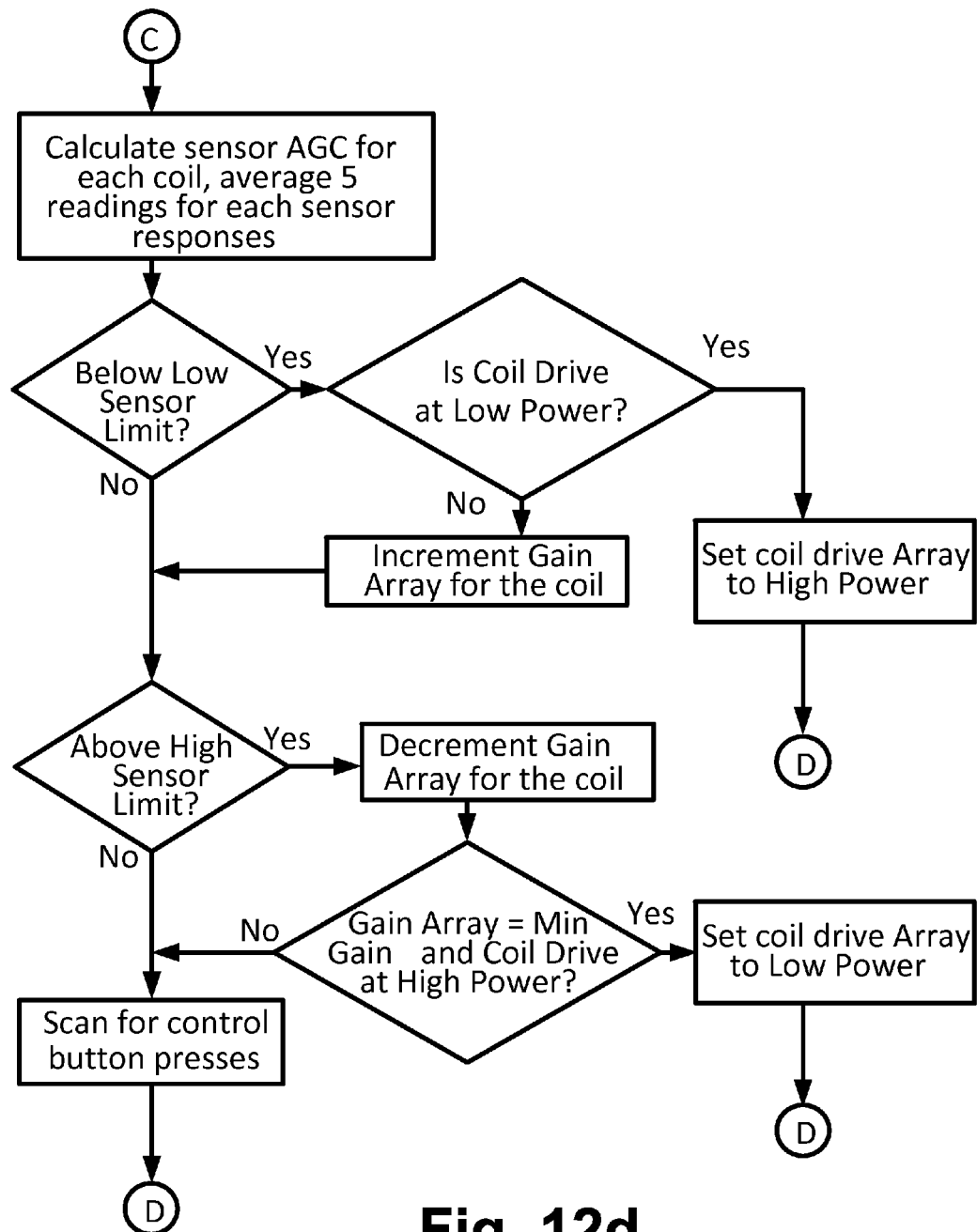
Figure 12E:
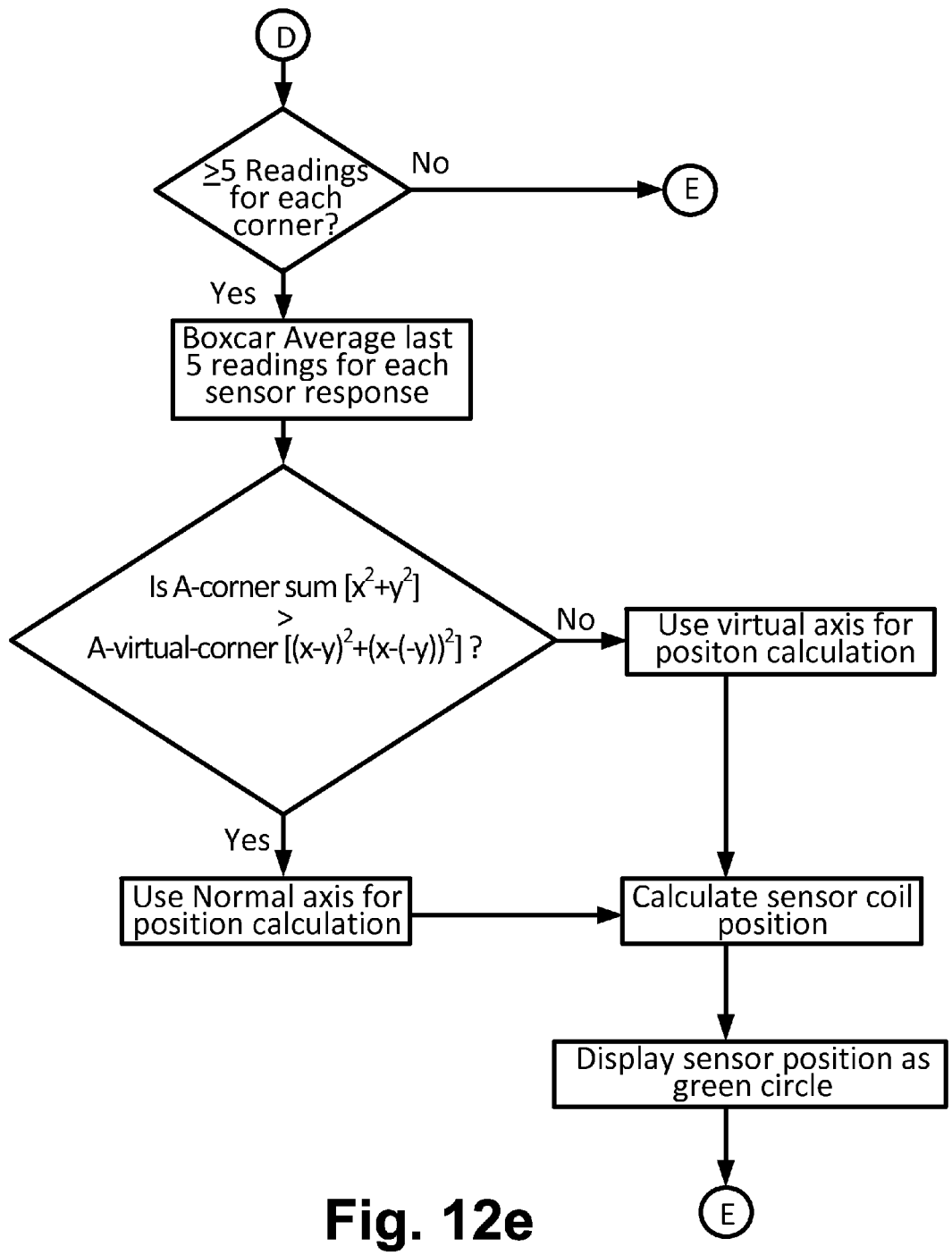
Figure 12F:
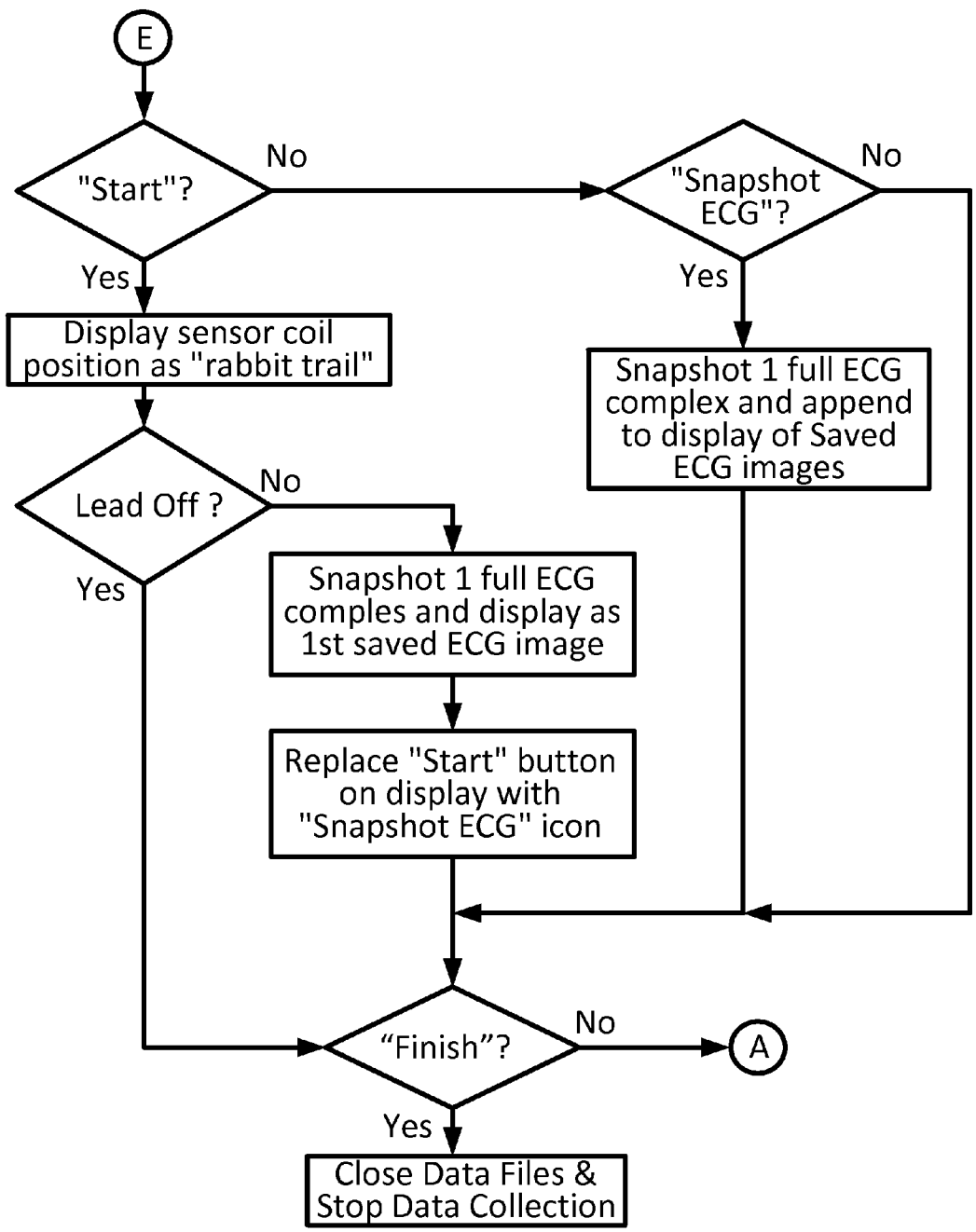

FIG. 11 is a detailed block diagram of a patient drive block 36, 60 (FIGS. 1, 7). A simpler version/option of a patient drive block 36 does not have ECG therefore no ECG leads; whereas, patient drive block 60 may include two ECG leads with patient isolation. The drive coil drive system in this diagram illustrates a two-coil virtual drive capability allowing the computer software to simultaneously drive two coils at select power levels. Such a system can include one or more of a voltage regulator, a watchdog switch, a drive switch, a power isolator, a voltage monitor, a cable buffer, a filter, an analog to digital converter, a phase adjuster, a demodulator, a signal filter, a programmable gain amplifier, a coil isolator, a coil sensor coil amplifier, a detector, memory, flash memory, a multiplexor, a polarity inversion switch, and/or the like. Each of these components can include cables or connectors for one or more of a coil interface, a power supply, a serial interface, a control interface, a status interface, an ECG interface or lead, an oscillator interface, a processor interface, a computer interface, a data interface, a network interface (cable or wireless), an internet interface, a video interface, a touchscreen interface, an SBC control or power interface, a board interface, a sensor interface, and/or the like as described herein or as known in the art.

FIGS. 12a-f provide an overview of a software functionality for a medical device location system hereof.

Figure 13:
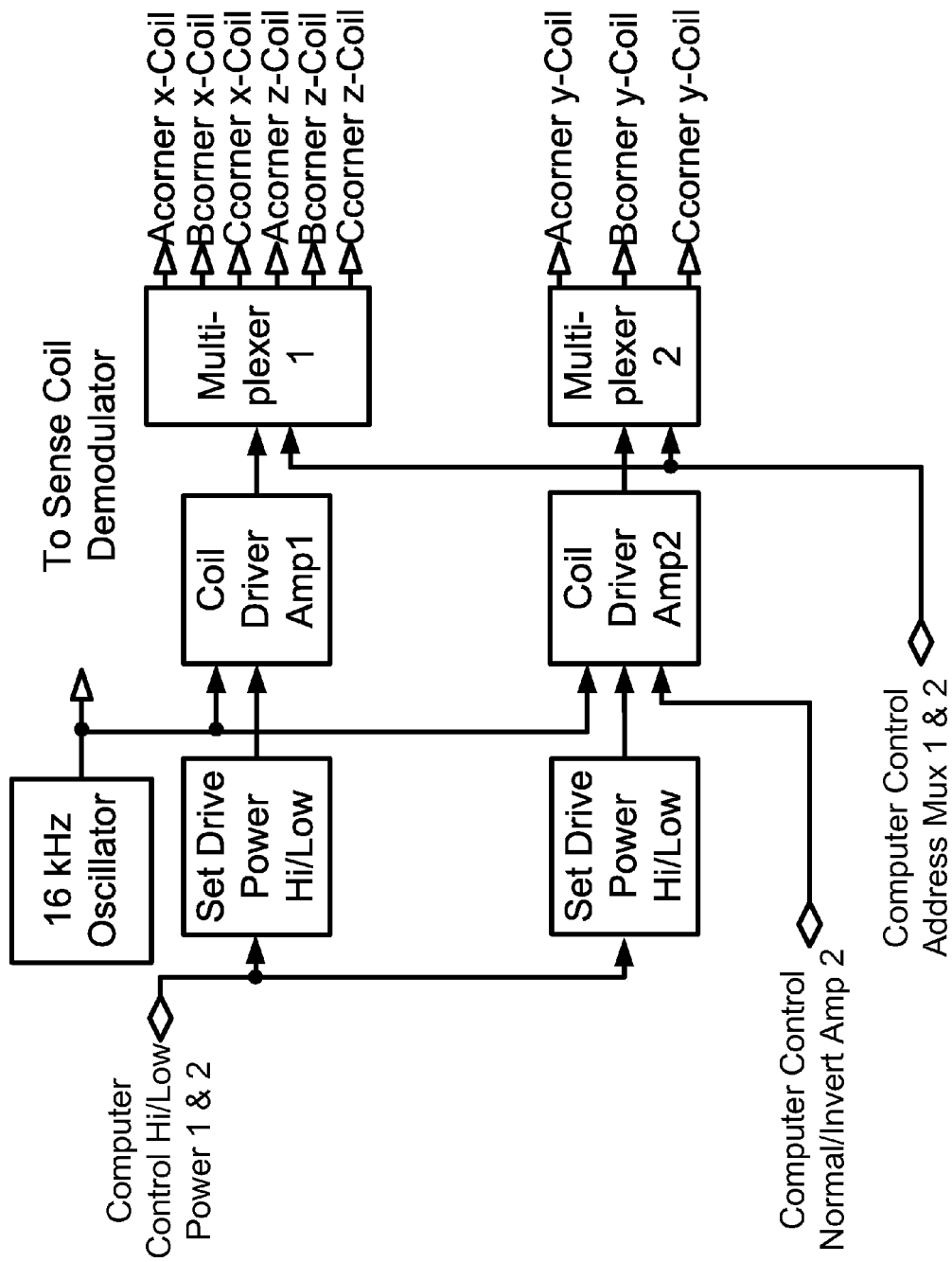
FIG. 13 is a detailed block diagram of a function of a coil drive with virtual x-y capability.

FIG. 13 is a simplified virtual coil drive system located on a patient drive block 36, 60. A coil driver hereof may have only two coil drives and only high/low power selection instead of a power control DAC. In this drive system it is possible to generate x-y and x-(-y) virtual coil drive (see FIG. 5) and also z-y and z-(-y) drive (see FIG. 6). One additional feature of this drive is a low power setting which allows drive power reduction if the sensing coil is too close to the drive coil (see software flow chart FIG. 12d). It also is possible to have two additional virtual vectors in this drive system by driving x-high-power together with y-low-power or driving x-low-power with y-high-power. Here, driving x-low-power together with g-low-power yields the same virtual axis—forty-five degrees from x and y axes—as driving both at high power.

Figure 14:
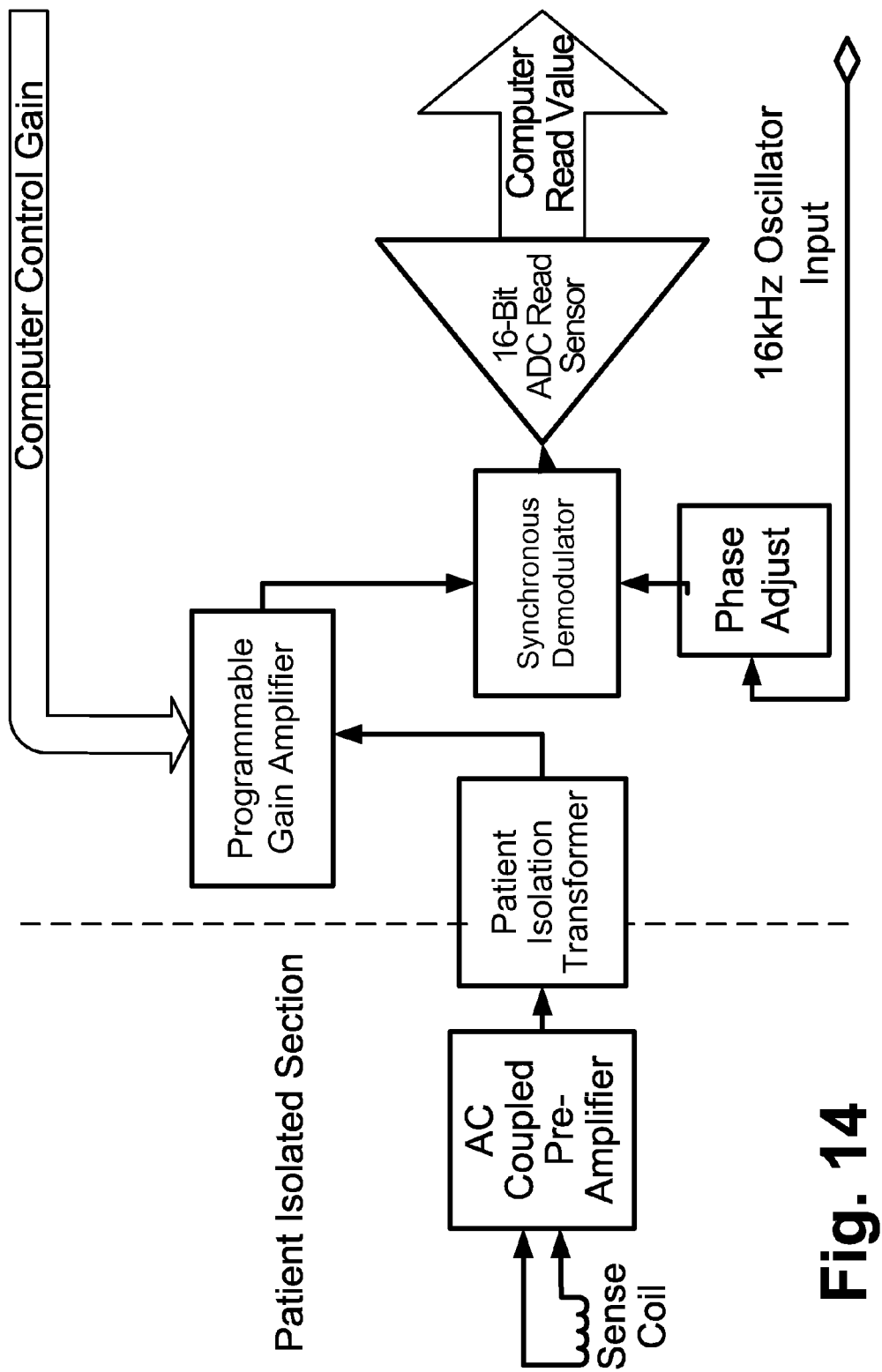
FIG. 14 is a detailed block diagram of sensor coil signal processing.

FIG. 14 is a detailed view of the sensor coil processing system of the main interface board 68. The sensor coil 30 on the guide wire or stylet can be connected through a cable 34, 54 to the main interface board 68. This sensor coil input is pre-amplified and filtered then passed through a patient isolation transformer to a software-controlled programmable gain amplifier. This amplified signal is then demodulated using the low frequency (e.g. 16 kHz) drive oscillator. The software then reads the sensor coil value with a high resolution (e.g. 16 bit or higher resolution) analog to digital converter (ADC). This read value for each drive coil activated and this value is proportional to the magnetic field measured by the sensor coil during that drive coil activation.

Figure 15:
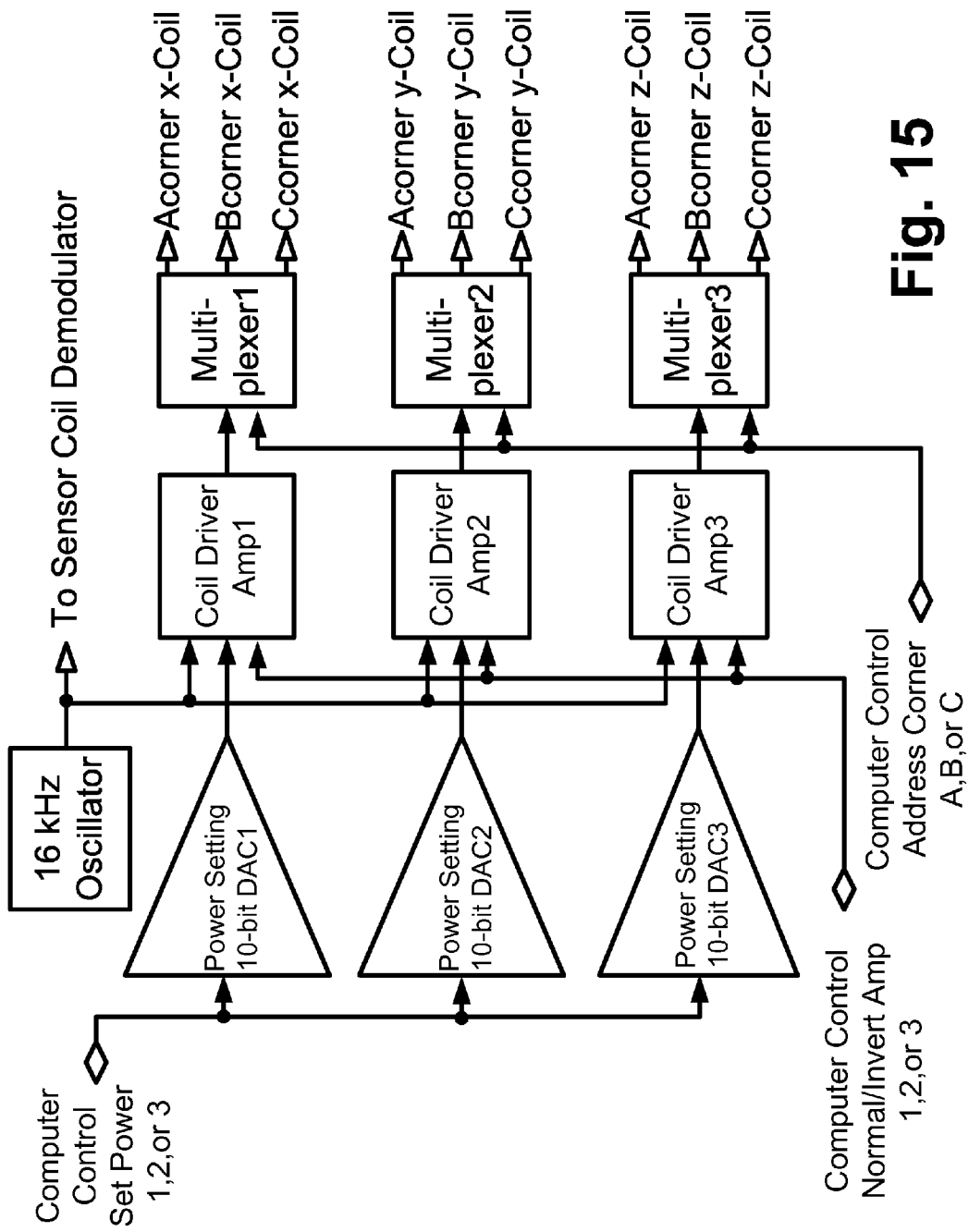
FIG. 15 is a detailed block diagram of a function of a coil drive with full virtual x-y-z capability.

FIG. 15 is a detailed view of a more complex virtual drive system. This drive system allows the x-axis coil 42, the y-axis coil 38 and z-axis coil 40 to all be driven simultaneously at independent power levels set by computer control through individual digital to analog converters (DAC). In this drive system, the virtual magnetic vector is the vector sum of x-axis drive plus y-axis drive plus z-axis drive. This virtual drive permits the virtual vector to point to any polar coordinate in space, and thus use polar coordinates as an option; however, it may often still be preferable to use a set of three orthogonal "virtual" axes to calculate the sensor coil 30 position.

Figure 16A:
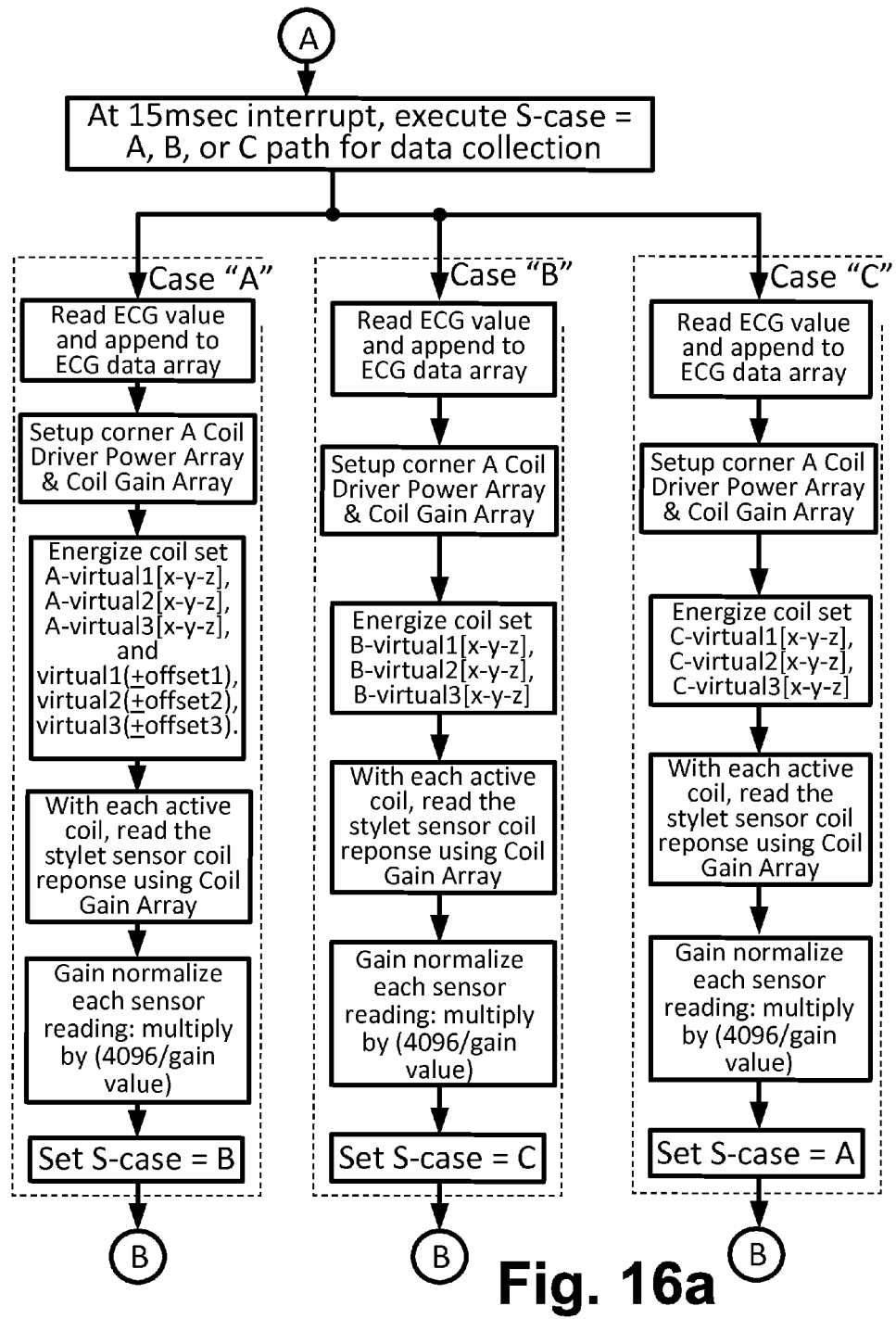
FIG. 16a-16c detail some algorithm alternatives for controlling the acquisition and display of sensor coil position in virtual x-y-z system.
Figure 16B:
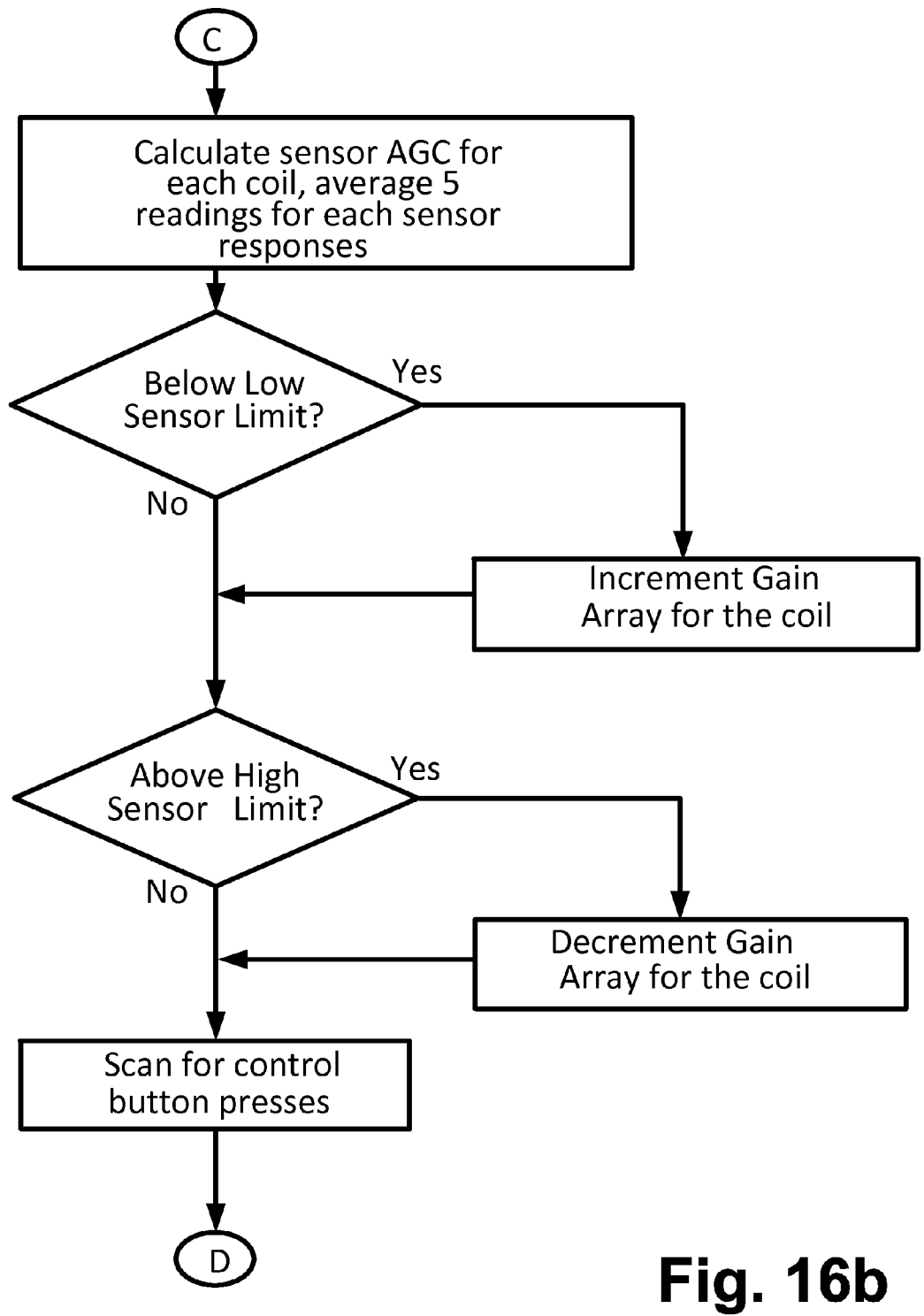
Figure 16C:
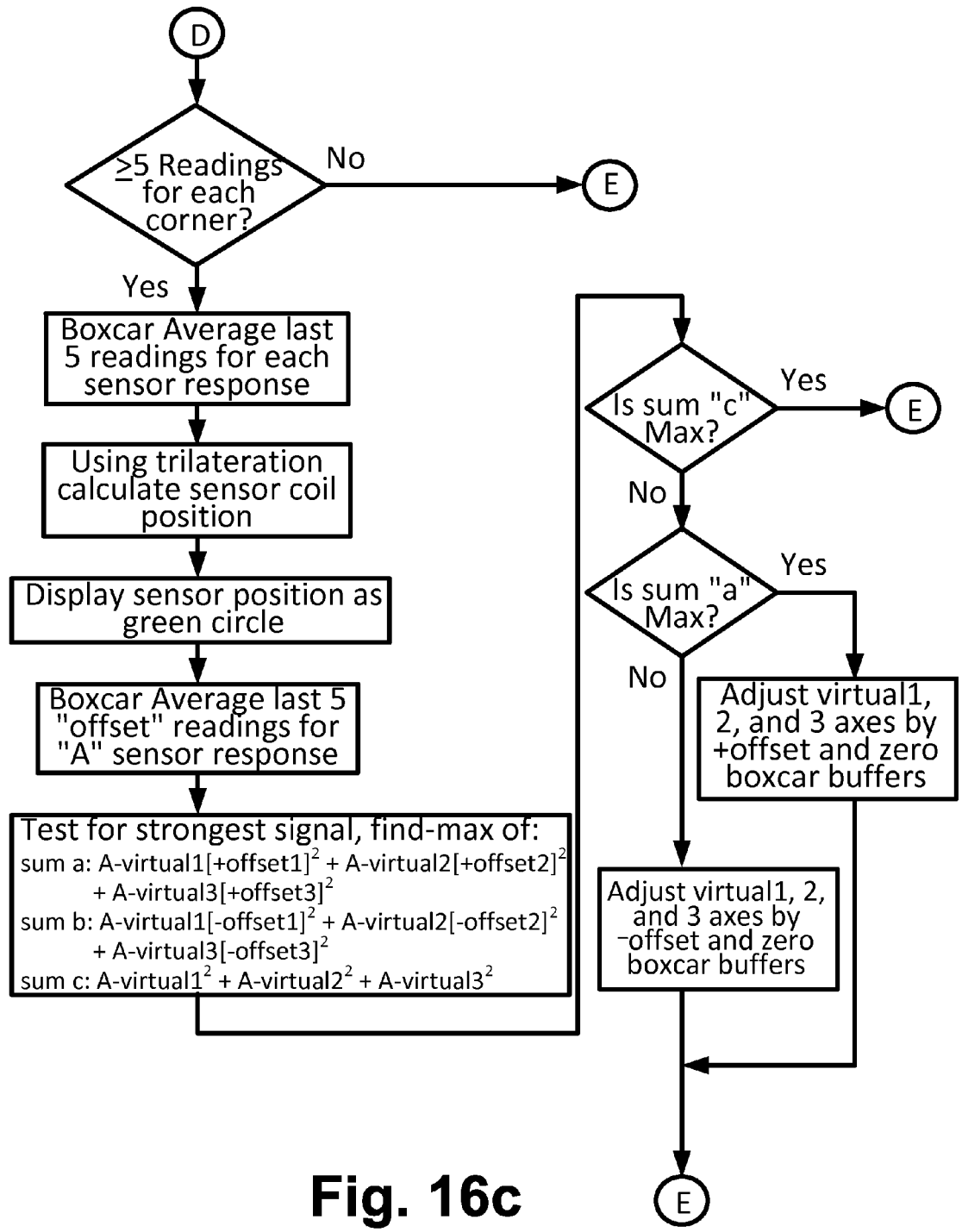

FIGS. 16a-c are a software flow chart showing changes drive and sensor coil processing for a fully independent x-y-z virtual drive system (see FIG. 15). This software adds a positive offset test and a negative offset test to the virtual axes for the A-corner coils. If the sensor coil response is stronger for an offset axis (FIG. 16c) than the current virtual axes, the system shifts to use the offset axes.

DETAILED DESCRIPTION

An aspect of the present developments is to provide an accurate system to generate a three-dimensional indication of location, position, orientation and/or travel of a medical device such as a guide wire or a catheter or stylet placed within a patient. This can in some implementations include a display of the location and/or travel of the device. A system hereof can include a sensor coil which is disposed in or on the tip of a guide wire or stylet cable, this sensor coil being communicatively cooperative with an external control and/or display box which may also be communicatively connected with an array of three-axis drive coils placed in some implementations in a triangular block on the patient's chest. This is also sometimes referred to as a drive block or an emitter block. The block contains the coil-drive controller that facilitates driving single coils, or pairs of coils, or triplets of coils together. The pair driving allows x-y, x-z, or y-z coils in a corner to be energized at the same frequency and same power creating a virtual drive axis at a 45 degree angle between the axis pairs. The coil-drive may also have an additional control to invert the drive waveform (shift the phase 180 degrees). This inversion of one coil in the pair can create a virtual drive axis at −45 degrees, thus creating an orthogonal pair of virtual axes within a plane. For example, the virtual x-y and x-(−y) are in the same plane as the x and y axes but rotated 45 degrees within the plane. This paired drive scheme improves the measurement accuracy of the system, especially when the sensor inside the catheter tip is substantially or exactly perpendicular to a normal coil drive axis. The system controller sequentially drives/energizes each coil, then each pair of coils while measuring the sensor coil response. When the sensor coil is nearly perpendicular to a drive axis there is significantly diminished response; thus, the virtual axis measurement will provide more accurate data for the position algorithm. Algorithms within the controller can be used to select the best data sets—regular x-y-z axis or virtual x-y-z axis—to calculate the sensor/medical device (e.g., catheter tip) location, position and/or orientation. A display can be used to show the catheter tip location as a position track of x-y location plotted over time plus an indicator for the z-axis, depth of the catheter. Depth could also be indicated by a variety of methods, as for example by thickening the position line segment in the plot as z decreases and thinning the position line segment as z increases. Alternatively, depth can be displayed as a lateral or "depth" view as a position track of y-z location plotted over time.

It is possible to extend this system further using programmable current control to the coil-driver circuit. Here, a virtual axis could be created at any angle between a magnet pair in a corner by energizing two magnets at the same frequency but with different current drive (power) levels to yield a vector-sum virtual axis at any angle between 0 and 90 degrees and inverting one coil in this drive scheme to yield a vector-sum virtual axis at any angle between 0 and −90 degrees. However, an orthogonal set of axes would typically still be selected to accurately locate the sensor coil. A further extension to this system could include energizing all three electromagnetic coils, x-y-z, together in a corner using the programmable current controls and inversion controls. The result here would be a vector sum from x-drive, y-drive, and z-drive coils that creates a virtual drive at any vector within three-dimensional space.

It is also possible to enhance this system with the integration of electrocardiogram (ECG) display with the location system. Here two reference electrodes may be plugged into or otherwise connected to the triangular patient block with the third electrode connected to the stylet or guide wire. An ECG may then be displayed for the user, so that P-wave changes, or other waveform changes can be shown to indicate proximity of the stylet or guide wire to the heart.

An aspect of the present developments is an electromagnetic medical device locating system for locating a medical device or the end or the tip thereof in a subject, including one or more of:

three or more triplet drive coil sets, each drive coil set including at least three orthogonally arranged discrete drive coils, each of the discrete drive coils being electromagnetic (EM) coils;
at least one sensor coil;
one or more system components that one or both provide drive signals energizing said discrete drive coils and measure resulting sensor coil response signals;
wherein the provision of drive signals includes one or both:
(i) sequentially driving one or pairs of said discrete drive coils within a triplet drive coil set; and
(ii) selectively providing phase inversion of the drive signal to any one or pairs of said discrete drive coils within a triplet drive coil set;
a computing component for calculating sensor coil disposition in the subject relative to said triplet drive coil sets from one or more measured resulting sensor coil response signals.

Another aspect may include: (a) three or more virtual or actual x-y-z axis electromagnetic (EM) triplet drive coils, each including at least three virtual or actual EM drive coils arranged in perpendicular axis to each other along an x-y-z axis, the virtual or actual EM triplet drive coils placed in a two- or three-dimensional geometric array; (b) at least one medical device sensor coil in physical association with at least one medical device tip and connected to at least one demodulator circuit; (c) at least one AC drive controller that (i) drives sequentially one or more of the virtual or actual EM drive coils; and (ii) provides a phase shifted signal to the demodulator; (d) at least one demodulator circuit including at least one demodulator for measuring the sensor coil output signal using frequency correlation with at least one AC coil driver signal from the AC drive controller to provide a synchronously demodulated sensor coil signal; (e) at least one automatic gain control circuit that maximizes the demodulated sensor coil signal; (f) a computing component for normalizing the resultant demodulated sensor coil signal data by dividing or multiplying the determined programmable gain value from the measurement of the demodulated sensor coil signals; (g) a computing component for selecting and calculating the optimized demodulated sensor coil signal data set generated from demodulated sensor coil signals, which optimized coil signal data set is calculated based on the sum of measured squared terms that have relatively higher or highest values; (h) a calculator for calculating the distance of the sensor coil and medical device tip from three or more virtual or actual EM triplet drive coil locations using the optimized demodulated sensor coil data set calculated using intersection of the spheres to provide the location of the sensor coil and corresponding medical device tip in space relative to the location of two or more of the virtual or actual EM triple drive coils provided in the two- or three-dimensional geometric array corresponding to the location of the medical device tip in the subject; and in some implementations, (i) a display. The result is the actual location of the medical device tip in the subject indicating height, width, and depth of the medical device tip in the subject calculated relative to the position of the drive coil geometric array.

It is possible to extend this system to include wherein one or more of (i) the virtual or actual EM drive coils or the virtual or actual EM triplet drive coils are arranged outside at least one of a two dimensional plane defined by at least three of the virtual or actual EM triplet drive coils; and/or (ii) at least four of the virtual or actual EM triplet drive coils form a tetrahedron as part of the three-dimensional geometric array.

It is possible to enhance such a system to include one or more of wherein (i) the display displays the relative location of the sensor coil or the medical device tip as a tracking of the sensor coil or medical device tip location over time; (ii) the display displays the sensor tip angle graphically for the user of the system, wherein the medical device tip angle is the angle of maximum response of the sensor coil as measured from sweeping the virtual drive axis through x-y plane (e.g. 0 to 360 degrees) then using this x-y maximum response angle as a vector added to the sweep through the virtual z axis; and/or (iii) the display displays the sensor tip angle graphically for the user of the system, wherein the medical device tip angle is the angle perpendicular to the angle of minimum response of the sensor coil as measured from sweeping the virtual drive axis through x-y plane (e.g. 0 to 360 degrees) then using this x-y minimum response angle as a vector added to sweep through the virtual z axis.

It is possible to extend such a system to further include wherein the intensity or power of current running through one or more adjacent EM drive coils in at least one of the EM triplet drive coils is programmable or adjustable using a control box including a programmable computer.

An aspect of the present developments is to provide a system wherein one or more of the EM drive coils are provided as the virtual EM drive coils, and wherein: (a) one or more controllers that select pairs or triplets of drive current values of the EM drive coils at regular time intervals to provide one or more paired magnetic drive coil vector values at angles from 0 to 90 degrees and phase inversion of at least one of the corresponding EM drive coils in at least one pair of the paired or tripled magnetic drive coil vectors to further provide one or more magnetic drive coil vector values at angles from −90 to 0 degrees; (b) one or more controllers that: (i) determine the angle values of maximum and minimum sensor coil responses within a plane using paired coil programmable current drive sweeping a range from 0 to 90 degrees; and (ii) that then determine the angle values of maximum and minimum sensor coil responses within a plane using paired coil programmable current drive sweeping using inverted phases of at least one coil and sweeping a range from −90 to 0 degrees; and/or (c) a calculator that: (i) computes at least one set of optimal virtual drive x and y axes for at least two of the EM triplet drive coils as values corresponding to plus and minus 45 degrees from the maximum and minimum sensor coil responses; and (ii) computes an optimal virtual drive z axis orthogonal to the plane of the optimal virtual drive x and y axes to provide at least one optimal virtual EM triplet drive axes and at least one of the virtual EM triplet drive coils.

Such a system can be extended wherein the system includes a programmable coil drive current for each of x, y, and z drive coils driven; and wherein (a) the triplets of drive current values selected at regular time intervals are provided as (i) paired magnetic drive coil vector values at angles from 0 to 90 degrees in an x-y plane together with 0 to 90 degrees from the x-y plane to the corresponding z-axis; and (ii) as phase inversion of one or two paired magnetic drive coil vector values at angles from −90 to 0 degrees in an x-y plane together with from −90 to 0 degrees from the x-y plane to the corresponding z-axis; (b) the angle values of maximum sensor coil responses within a plane for both 0 to 90 and −90 to 0 degrees are fixed and used for at least two x and y virtual axes in a virtual plane and the values of maximum sensor coil response are determined for the corresponding virtual z axis to provide at least one maximum virtual x-y-z vector for at least one of the corresponding virtual EM triplet drive coils; (c) the angle values of minimum sensor coil responses within a plane for both 0 to 90 and −90 to 0 degrees are fixed and used for at least two x and y virtual axes in a virtual plane and the values of maximum sensor coil response are determined for the corresponding virtual z axis to provide at least one minimum virtual x-y-z vector for at least one of the corresponding virtual EM triplet drive coils; (d) the at least one optimal virtual EM triplet drive vector and at least one of the virtual EM triplet drive coils are generated using intermediate virtual drive x and y axes as plus and minus 45 degrees from the minimum virtual x-y-z vector and intermediate virtual drive z axis as orthogonal to the intermediate virtual drive x and y axis; the optimal virtual x, y, and z axis are then generated by pivoting the intermediate x, y, and z axes by moving the intermediate z axis 45 degrees about the maximum virtual x-y-z vector.

Such a system can be enhanced wherein the display further displays P-wave or other cardiac waveform changes over time in combination with the location of the medical device such as a guide wire or stylet tip in relationship to the subject's heart.

Such a system can be extended by further including (i) an x-axis tilt meter and y-axis tilt meter which uses gravity to measure the x-axis and y-axis tilt from true vertical; and (2) a computer to calculate and display the location of the medical device tip as height, width, and depth of the sensor coil corrected for the tilt the geometric array. Such a system can be enhanced wherein the geometric array and sensor coil connected to the display via a wireless interface.

Such system can be extended by further including an electrocardiogram (ECG) operably associated with the geometric array with a display to show the subject's ECG signal over time; or by further including an electroencephalogram (EEG) operably associated with the geometric array with a display to show the subject's EEG signal over time.

An aspect of the present developments can include a method for locating a medical device in a subject, including: (a) providing a system as presented herein; (b) inserting and positioning the medical device tip associated with a functional and sterile medical device into the subject; and (c) recording or monitoring the output of the display to locate the medical device tip in the subject.

Such a method can be extended wherein the method further includes the use of at least one selected an electrocardiogram (ECG), an electroencephalogram (EEG), an x-ray machine, an computer assisted tomography (CAT) machine, a positron emission tomography (PET) machine, an endoscope, or an ultrasound imaging device or composition.

Methods, Computer Systems and Software

An aspect of the present developments can include methods, computer systems and software, provided as programming code or instructions on computer readable media or hardware or networks or computer systems, for generating virtual electromagnetic (EM) triplet drive coils for generating data corresponding to the location coordinates for a sensor coil, including:

(a) electronically providing triplets of drive current values generated from at least three EM drive coils of the EM triplet drive coils in detectable proximity to the EM sensor at regular time intervals to provide one or more paired magnetic drive coil vector values generated at angles from 0 to 90 degrees without and from −90 to 0 degrees with phase inversion;

(b) electronically providing angle values of maximum or minimum EM sensor coil responses generated from the EM triplet drive coils within the x-y plane using paired x-y coils' programmable current drive sweeping a range from 0 to 90 degrees without and from −90 to 0 degrees with phase inversion;

(c) electronically computing at least one set of optimal virtual drive x and y axes as values corresponding to plus and minus 45 degrees from the maximum or the minimum sensor coil response;

(d) electronically computing an optimal virtual drive z axis orthogonal to the plane of the optimal virtual drive x and y axes to provide at least one optimal set of virtual EM triplet drive axes for at least one of the EM triplet drive coils.

Such a method can be extended wherein (a) the triplets of drive current values selected at regular time intervals are provided as (i) paired magnetic drive coil vector values at angles from 0 to 90 degrees in an x-y plane added together with coil vectors of the z-axis from 0 to 90 degrees from the x-y plane; and (ii) as phase inversion of one or more paired magnetic drive coil vector values at angles from −90 to 0 degrees in an x-y plane added together with coil vectors of the z-axis from −90 to 0 degrees from the x-y plane; (b) the angle value of maximum sensor coil response within the x-y plane for both 0 to 90 and −90 to 0 degrees is determined as the intermediate virtual maximum x-y axis and this intermediate virtual maximum x-y axis added to the z-axis swept from 0 to 90 and −90 to 0 degrees to determine at least one maximum virtual x-y-z vector for at least one of the corresponding EM triplet drive coils; (c) the angle value of minimum sensor coil response within the x-y plane for both 0 to 90 and −90 to 0 degrees is determined as the intermediate virtual minimum x-y axis, and this intermediate virtual minimum x-y axis is added to the z-axis swept from 0 to 90 and −90 to 0 degrees to determine at least one minimum virtual x-y-z vector for at least one of the corresponding EM triplet drive coils; and (d) the at least one optimal virtual EM triplet drive axes for at least one of the EM triplet drive coils are calculated using plane defined by the maximum virtual x-y-z vector and minimum x-y-z vector wherein the optimal virtual drive x and y axes are plus and minus 45 degrees from the minimum virtual x-y-z vector and the optimal virtual drive z axis as orthogonal to the optimal virtual drive x and y axes.

FIG. 1 is an overview schematic diagram of an implementation of the present developments. A control box 20 contains a touch screen display 22 with a computer control and data processing. The triangular patient drive block 36 is connected via power and communications cable 26 to the control box 20. The drive and sensor electronics 28 may be located in the block 36 and provide drive coil control and sensor coil demodulation/amplification. In the three corners of the block 36 are mounted each triplet drive coil set 24 (24a, 24b, 24c). Alternatively, each coil set 24 could be mounted as feet protruding from the bottom of the block 36. The sensor coil 30 is built onto a small diameter biocompatible cable 32 which may be inserted into a medical device such as a catheter to be placed in the patient. The sensor signal is connected back to the control box 20 with a two-wire cable 34. FIG. 3 provides a detailed view of a sensor coil 30. Sensor coil performance can be improved by winding the coil about a ferromagnetic wire in the tip of the cable 48. The ferromagnetic material should be used for the length of the sensor coil 30 and may be followed by non-ferrous material. Two fine wires 50 from the sensor coil 30 are attached or associated (e.g., glued or wrapped) and sealed 49 down the length of the cable 48.

As presented, e.g., in FIG. 8, an aspect of this device may include continuous display at the position of the sensor coil 30 placed in the tip of a medical device as the medical device moves through the patient's tissue. The patient drive block 36, 60, is placed over the patient's body where the medical device will be targeted (e.g., over the chest preferably aligned with the sternal notch if the medical device will be placed in the area of the heart).

As presented, e.g., in FIG. 1 and FIG. 7, respectively, the sensor coil cable 34, 54 and patient drive block cable 26, 56 are connected to a user control box 20. The user control box 20 contains a computer 68 (FIG. 9) which sequentially drives each driver coil 38, 40, 42 (FIG. 2) on each axis in every corner 24a, 24b, 24c of the patient drive block 36, 60. The coil driver creates magnetic drive vectors as shown in FIG. 4, 5, or 6—where FIG. 4 represents normal drive and FIGS. 5 and 6 represent virtual drive. The single board computer 68 (FIG. 9) measures the demodulated output signal from the sensor coil 30 for each sequentially driven coil 24 (FIG. 1). The single board computer 68 (FIG. 9) continuously adjusts the gain of each output signal using a programmable gain stage in the demodulator electronics and scales all the sensor data to be gain normalized (see FIG. 12b). Here, gain normalized means that if a measured response is value "a" collected at a programmable gain of "4.00" times, then the normalized resultant value is "a" divided by 4.00. A non-limiting example of an alternative gain normalizing method is to multiply each value "a" by 4096/gain, e.g. "a"×4096/4.00. The programmable gains that can be used as a non-limiting example are 1.00, 2.00, 4.00, 8.00, 16.00 and 32.00 plus there can be a final gain stage that is selectable for 1.00 or 1.41 (equivalent to 1/$\sqrt{2}$). Examples of a resultant set of programmable gains are 1.00, 1.41, 2.00, 2.82, 4.00, 5.64, 8.00, 11.28, 16.00, 22.56 and 32.00.

From the normalized response data, the single board computer 68 (FIG. 9) compares the sum of the squares of the sensor's normal response to the sum of the squares of the sensor's virtual response. Whichever sum is greater or has the stronger response can be used by the computer 68 to calculate the sensor coil 30 location using trilateration which is the calculation of the intersection of three spheres where each sphere is defined as the radial distance of the sensor coil 30 from each x-y-z driver coil set 24a, 24b, 24c (FIG. 1).

From each corner, the radial distance can be defined as a constant divided by the 6$^{th}$ root of the sum of the squares of the x, y, and z measured normalized response. Here the constant, k, is a calibration constant reflecting the strength of each drive coil 38, 40, 42 (FIG. 2) and the sensitivity of the sensor coil 30 (FIG. 1). In one possible aspect, a calibration constant could be generated during manufacturing for each of the drive coils and then stored as calibration constants for each coil in non-volatile memory of the patient drive block. By trilateration, the radial distance equation for each corner is:

$$r = k/\sqrt[6]{(x^2+y^2+z^2)}$$

The sensor coil location is then calculated from three equations for the three corners of plate 36:

$$r_1^2 = k^{2/3}\sqrt[3]{((x_1^2+y_1^2+z_1^2))}$$

$$r_2^2 = k^{2/3}\sqrt[3]{((x_2-d)^2+y_2^2+z_2^2)}$$

$$r_3^2 = k^{2/3}\sqrt[3]{(x_3^2+(y_3-d)^2+z_3^2)}$$

Here d is the distance of each coil from the other and k is the calibration constant which scales the result into meaningful units of distance, e.g. centimeters or inches. In this non-limiting example, the coils on the patient drive plate or block 36, 60 (FIGS. 1 and 7) are arranged in a right triangle, with two sides of equal length, d, as reflected in the 2$^{nd}$ and 3$^{rd}$ equations above, just on different axis, x or y. The solution to these equations yielding the sensor coil location is:

$$x_S = (r_1^2 - r_2^2 + d^2)/2d$$

$$y_S (r_1^2 - r_3^2 + d^2)/2d$$

$$z_S = +/-\sqrt[2]{(r_1^2 - x_S^2 - y_S^2)}$$

Here the solution for z (vertical axis) is assumed to be negative as the sensor coil 30 cannot be above the plane of the patient drive block 36, 60 (FIGS. 1 and 7) unless it is outside the patient.

While the above reflects one non-limiting approach to locating the sensor coil 30 (FIG. 1), it is not the only or optimal for coil location. Specifically when the sensor coil 30 is nearly perpendicular to a driver coil axis the sensor coil response approaches zero; therefore a "virtual axis" drive system provides for the optimal sensor coil response. In this approach the coil driver circuit is designed to selectively drive, within a triplet set, pairs of coils, e.g. 38 and 42 (FIG. 2), together at the same frequency and amplitude with an additional driver control to selectively invert the phase of one coil in the pair. This paired coil drive of x-y coils creates the 1st virtual axis at forty-five degrees from the original x and y axes. The paired coil drive is then operated with x-(−y) which drives the x-coil together with inverted-phase y-coil and this creates the $2^{nd}$ virtual axis at minus forty-five degrees from the original x and y axes. The result is two orthogonal virtual magnetic vectors as shown by the dashed lines in FIG. 5 for x-y paired coil drive or in FIG. 6 for y-z paired coil drive. For paired drive, the single board computer 68 (FIG. 9) sequentially drives the x-y pair, x-(−y) pair, and z axis for each x-y-z coil set 24a, 24b, 24c (FIGS. 1 and 7). Here, "(−y)" means inverted phase on y axis drive. The measured sensor coil response for paired-coil drive must be scaled down by 1.4142 because of vector summing of the two coils driven together. Alternatively, the coil-driver power could be scaled down by 0.7071 in hardware when driving pairs so that the vector sum of two coils equals the magnetic vector of a single coil drive. The single board computer 68 measures the sensor coil response for each corner in normal drive and paired drive, and then selects the strongest signal from each corner comparing the sum of $x^2$, $y^2$, and $z^2$ normal coil drive response to the sum of $(x-y)^2$, $(x-(-y))^2$, and $z^2$ paired coil drive response. The strongest signal from each corner is used to calculate the location of the sensor coil 30 using the trilateration method described in the above equations. This example illustrates paired x-y coil drive; and by logical extension this may also apply to x-z, or y-z paired drive. An objective in some implementations of these developments may include improving the accuracy of horizontal (x-y) location; therefore the paired x-y drive can be preferred over x-z or y-z.

An improvement of the paired-coil drive can be to add programmable (DAC) power control to the coil drivers on the drive coil drive electronics board 28 (FIG. 11). Here, the single board computer 68 (FIG. 9) has the capability to select pairs of drive current power settings which steer the virtual axis of the paired coils from 0 to 90 degrees. Inversion of one of the coil drivers in the pair provides the capability for virtual axis from −90 to 0 degrees. In this design, the single board computer 68 selects pairs of power settings output to the x-y paired coil driver to sweep the virtual drive axis from 0 to 90 degrees while recording the sensor coil response and this process is repeated with the y coil driver phase inverted to sweep from −90 to 0 degrees. The angle of the virtual axis when the sensor coil response data is maximum indicates the sensor coil 30 (FIG. 1) is parallel to the virtual axis and the angle of the virtual axis when the sensor coil response data is minimum indicates the sensor coil 30 is perpendicular to the virtual axis. Here the maximum angle and minimum angle are orthogonal (perpendicular). The single board computer 68 (FIG. 9) calculates the optimum virtual x axis at forty-five degrees from the measured angle for maximum (or minimum) response and calculates the optimum virtual y axis as an angle orthogonal to the virtual x axis. As all x-y-z coil sets 24a, 24b, 24c are mechanically aligned the solution for best virtual axes in one corner applies to all corners in the patient drive block 36, 60 (FIGS. 1 and 7). The single board computer 68 (FIG. 9) measures the sensor coil response for all corners using these optimum virtual x axis, optimum virtual y axis plus normal z axis. The sum of $(virtual\ x)^2$, $(virtual\ y)^2$, and $z^2$ sensor coil responses for each corner is used to calculate the position of the sensor coil 30 (FIG. 1) using the trilateration method described in the above equations. This example illustrates paired x-y coil drive; and by logical extension this also applies to x-z, or y-z paired drive; however, the preference in this development is to improve accuracy of horizontal location and thus use paired x-y drive.

An alternative, non-limiting, method for finding the optimum virtual x and virtual y axis in the programmable pair-coil drive above is to use successive approximation instead of sweeping 0 to 90 degrees. In this approach, the single board computer 68 (FIG. 9) has the capability to select pairs of drive current power settings which steer the virtual axis from −90 to +90 degrees. The single board computer first tests the sensor coil response to the paired coils at virtual axes +45 and −45 degrees and selects the virtual axis with the stronger response. Using the stronger axis, the computer then tests the sensor coil response to paired coils at +22.5 and −22.5 degrees from the current virtual axis and selects the virtual axis with the stronger response. This process continues for +/−11.25 degrees, +/−5.625 degrees, until the limits of drive power resolution are reached. The resulting virtual axis is the axis of maximum response. The single board computer 68 calculates the optimum virtual x axis at forty-five degrees from the measured angle for maximum response and calculates the optimum virtual y axis as an angle orthogonal to the virtual x axis.

A selection of the best set of virtual axes can be accomplished with a triplet-coil drive scheme, with programmable power control to the coil drivers for each axis, and with the driver control to selectively invert the phase of any coil in the triplet x-y-z coil sets 24a, 24b, 24c (see FIG. 15). Here, the single board computer 68 (FIG. 9) has the capability to select pairs of drive current power settings which steer the x-y virtual axis of the paired coils from 0 to 90 degrees. Inversion of one of the coil drivers in the pair provides the capability for x-(−y) virtual axis from −90 to 0 degrees. With the addition of the third coil drive and inversion the single board computer 68 can sweep the virtual axis 0 to 90 and −90 to 0 degrees in z range. The microcomputer selects pairs of current settings output to the x-y paired coil driver to sweep the virtual drive axis from 0 to 90 degrees while recording the sensor coil response and this process is repeated with the y coil driver phase inverted to sweep from −90 to 0 degrees. The angle of the x-y virtual axis when the sensor coil response data is maximum indicates the sensor coil 30 (FIG. 1) is parallel for the x-y plane. The single board computer 68 then sets this x-y axis and sweeps the z axis drive from −90 to 0 and 0 to 90 degrees while recording the sensor coil response. The polar angle of the x-y-z virtual axis when the sensor coil response data is at maximum indicates the sensor coil 30 is parallel to this virtual x-y-z axis. The single board computer 68 then repeats this process to find the minimum sensor coil response sweeping x, y, and z axes. The polar angle of the x-y-z virtual axis when the sensor coil response data is minimum indicates the sensor coil 30 is perpendicular to this virtual x-y-z axis. These two vectors, virtual minimum and virtual maximum, define a plane intersecting the sensor coil 30. For optimum response, the single board computer 68 calculates a virtual x axis 45 degrees between the maximum and minimum vectors, then calculates the virtual y axis as 90 degrees from the virtual x in the plane defined previously. Here virtual z axis is defined as orthogonal to the plane of virtual minimum and virtual maximum vectors. The single board computer 68 then tilts the virtual z axis and the plane of virtual x axis and virtual y axis 45 degrees toward the virtual minimum vector, and the result is the optimal virtual axis set which maximizes the sensor coil response. As all x-y-z coil sets 24a, 24b, 24c are mechanically aligned the solution for best virtual axes in one corner applies to all corners in the driver array. The single board computer 68 measures the sensor coil response for all corners using these optimum virtual x, y, and z axes. The sum of (virtual x)$^2$, (virtual y)$^2$, and (virtual z)$^2$ sensor coil responses for each corner may be used to calculate the sensor coil 30 using the trilateration method described in the above equations. One method to maintain the optimum x-y-z axis over time is to continuously test the sensor coil response to small deviations (offset angle) from the optimum axis (see FIG. 16c). Here, the single board computer 68 compares the sum of (virtual x)$^2$, (virtual y)$^2$, and (virtual z)$^2$ sensor coil responses for the current virtual axis to the sum for virtual axis plus offset angle and the sum for virtual axis minus offset angle. The computer 68 then selects the axis with the largest summed response— this becomes the new optimum x-y-z axis and the process continues to iterate testing small deviations over time.

The single board computer 68 may then graphically display the sensor coil position on the display 22 of the control box 20. The position is continuously updated adding onto the previous graphical data to create a track or path of the sensor coil 30 over time. The user interface of the single board computer 68 allows the user to clear the recorded track or to save the recorded track to non-volatile memory. Touchscreens have been described; however keyboard or other data input, or user interface options may be used.

The construction details above for the control box 20 (FIGS. 1, 7) may provide for a tethered device with the display/control separate from the patient block 36, 60 (FIGS. 1 and 7). However, an alternative construction would be to build a device or system in which the patient block 36, 60 is battery-powered and connected wirelessly to the control box 20. In another variation, the control box 20 could be integrated into or as part of the patient block and placed on the patient chest or other locations to track medical device position. Wireless and/or wired connections are thus optionally available for the connections of the drive coil sets to the control or system components for the driving thereof; as well as for the connections of the sensor coil to the control or system components for measuring or receiving the response signals of the sensor coil.

An alternative construction would be to use four or more drive coils 24 oriented as a square, rectangle, pentagon, circle, oval, geometric, or any other suitable shape, in or as the patient drive block 36, 60 (FIGS. 1, 7).

An alternative construction (FIG. 7) is to optionally incorporate electrocardiograph (ECG) monitoring into the medical device location system to facilitate placement of the medical device with sensor coil 30 in close proximity to the heart. Here the patient drive block 60 may be modified with one or more ECG pads 64 and ECG lead wires 62 which attach to the patient's chest and the third ECG lead is provided by a conductive wire 52 added in or otherwise made part of the core of the guide wire or stylet sensor coil 30.

An ECG amplifier can be added to the main interface board 70 (FIG. 9), and the single board computer 68 may then present the ECG on the display 22 as the medical device such as a catheter is advanced within the patient's or subject's body. The user can observe changes in the P-wave or other wave elements of the ECG as the medical device/catheter reaches the heart. Ideally, the single board computer 68 could use a waveform analysis to assist the user in recognizing changes occurring to the P-wave or other waveforms.

A component to this design may include connecting the signals from the sensor coil 30 and ECG 52 to the user control box 20. This is complicated in practice by covering the entire patient and patient block 60 with sterile drapes for insertion of the patient's medical device/catheter. In this design, a miniature stereo phone plug or similar could be used to pierce a plastic bag and connect to cable 34, 54 a pigtail from the user control box 20.

Methods, devices and systems can thus be provided for one or both of two- or three-dimensional location of the disposition of a sensor coil in a subject including: an array of electromagnetic drive coil sets, each set having two or three dimensionally oriented drive coils; a sensor coil being electromagnetically communicative with the array of electromagnetic drive coil sets; and, a system controller communicative with and adapted to energize one or more of the electromagnetic coils in the array of electromagnetic drive coil sets, the energizing of the one or more of the electromagnetic coils including one or more of energizing the coils singly, or in pairs of x-y and y-z or x-z coils while measuring the response of the sensor coil; whereby the system uses the measurements of the responses of the sensor coil to calculate the location and orientation of the sensor coil relative to said drive coil sets.

This may include two- and/or three-dimensional location of a catheter in tissue using an array of x-y or x-y-z oriented electromagnetic coils, where a sensor coil can be associated with one or more catheter tips, and where the system controller can energize one or more external coils, such as but not limited to, pairs of x-y and y-z or x-z coils while measuring the response of the sensor coil; the system can use these sensor coil measurements to calculate the position and orientation of the catheter tip, and in some implementations, the system controller can graphically display the catheter tip position, depth and/or orientation, e.g., but not limited to, over time.

From the foregoing, it is readily apparent that new and useful implementations of the present systems, apparatuses and/or methods have been herein described and illustrated which fulfill numerous desiderata in remarkably unexpected fashions. It is, of course, understood that such modifications, alterations and adaptations as can readily occur to the artisan confronted with this disclosure are intended within the spirit of this disclosure which is limited only by the scope of the claims appended hereto.

We claim:

1. A medical device locating system for determining disposition of a sensor coil in a subject, said system comprising:
   a. an array of three or more triplet drive coil sets, each drive coil set including at least three orthogonally arranged discrete drive coils, each of the discrete drive coils being electromagnetic coils;
   b. at least one sensor coil;
   c. a first system component that provides AC drive signals energizing said discrete drive coils;
      wherein the provision of drive signals includes one or both:
      (i) simultaneously driving two or three said discrete drive coils at two or three separate current intensity or power levels within said triplet drive coil set to generate an electromagnetic field defining a virtual axis; and,
      (ii) simultaneously driving two or three said discrete drive coils within said triplet drive coil set with one, two or three drive signals with reversed phase;
   d. a second system component for sequentially energizing said discrete drive coils singly then as virtual pairs or virtual triplets and measuring the resulting single and virtual sensor coil response signals;

e. a computing component for calculating sensor coil disposition in the subject relative to said triplet drive coil sets from one or more measured resulting sensor coil response signals.

2. A system according to claim 1, further comprising a computing component for:

calculating sensor coil signal data sets generated from the measured resulting single and virtual sensor coil response signals;

selecting optimum sensor coil signal data sets from the calculated sensor coil signal data sets based on the sum of measured squared sensor coil data terms that have relatively higher values;

using said optimum sensor coil data sets in calculating the intersection of spheres to provide the disposition of the sensor coil relative to the respective locations of the three or more said triplet drive coil sets.

3. A system according to claim 1, wherein said at least one sensor coil is connected to at least one demodulator circuit within one or more of said one or more system components, and said demodulator circuit comprises at least one demodulator for measuring the amplitude of said sensor coil output signals to provide demodulated sensor coil signals.

4. A system according to claim 1, further comprising an automatic gain control (AGC) circuit within one or more of said one or more system components, and said automatic gain control circuit associated with and receiving one or more response signals from the sensor coil, the automatic gain control circuit maximizing the response signal before communicating said response signal to said one or more system components.

5. A system of claim 1, further comprising a display that shows the disposition of said sensor coil in said subject relative to the array of said triplet drive coils.

6. A system of claim 5, wherein the display displays said disposition of said sensor coil in said subject indicating height, width, and/or depth in said subject relative to said triplet drive coil sets.

7. A system according to claim 5, wherein said display displays the angular orientation of said sensor coil relative to said triplet drive coil sets.

8. A system of claim 5, wherein one or more of said sensor coils is in physical association with the tip of a catheter, guide wire or stylet; and said display displays said relative disposition of said sensor coil or said tip as a tracking of said sensor coil or tip location over time.

9. A system of claim 1, wherein the intensity or power of current running through one or more adjacent discrete drive coils in at least one or more of said triplet drive coils is programmable or adjustable using a control box comprising a programmable computer.

10. A system of claim 1, wherein one or more of said triplet drive coils are provided as said virtual pairs or virtual triplets, and wherein:

a. said first system component that provides AC drive signals further (iii) uses tables or calculated current settings to sequentially sweep virtual electromagnetic drive vectors from 0 to 90 degrees and −90 to 0 degrees for said x, y, and z axes;

b. said computing component further
  (i) determines angle values of maximum and minimum sensor coil responses within a plane using paired coil programmable current drive sweeping a range from 0 to 90 degrees;
  (ii) then determines the angle values of maximum and minimum sensor coil responses within a plane using paired coil programmable current drive sweeping using inverted phases of at least one coil and sweeping a range from −90 to 0 degrees;
  (iii) computes at least one set of optimal virtual drive x and y axes for at least two of said triplet drive coils as values corresponding to plus and minus 45 degrees from said maximum or minimum sensor coil responses; and
  (iv) computes an optimal virtual drive z axis orthogonal to the plane of said optimal virtual drive x and y axes to provide at least one optimal virtual triplet drive axes and at least one of said triplet drive coils.

11. A system of claim 10, further comprising a display that shows the location of said sensor coil in said subject relative to the array of triplet drive coils.

12. A system of claim 11, wherein the display displays said disposition of said sensor coil in said subject indicating height, width, and/or depth in said subject relative to said triplet drive coil sets.

13. A system according to claim 11, wherein said display displays the angular orientation of said sensor coil relative to said triplet drive coil sets.

14. A system of claim 1, wherein one or more of said triplet drive coils are provided as said virtual triplets, and wherein:

a. said first system component that provides AC drive signals further (iii) uses tables or calculated current settings to sequentially sweep the virtual electromagnetic drive vectors from 0 to 90 degrees and −90 to 0 degrees for all axes;

b. said computing component further
  (i) determines the x-y vector angle (XYMAX) of maximum sensor coil response within the x-y plane using paired coil programmable current drive sweeping a range from 0 to 90 degrees, and using inverted phase of at least one coil sweeping a range from −90 to 0 degrees;
  (ii) determines the x-y-z vector angle of maximum sensor coil response adding a sweep of z axis 0 to 90 and inverted −90 to 0 to the XYMAX vector;
  (iii) determines the x-y vector angle (XYMIN) of minimum sensor coil response within the x-y plane using paired coil programmable current drive sweeping a range from 0 to 90 degrees, and using inverted phase of at least one coil sweeping a range from −90 to 0 degrees;
  (iv) determines the x-y-z vector angle of minimum sensor coil response adding a sweep of z axis 0 to 90 and inverted −90 to 0 to the XYMIN vector; and
  (v) computes at least one set of optimal virtual drive x-y-z axes for at least one of said triplet drive coils as virtual x axis and virtual y axis corresponding to a 45 degree rotation in the virtual x-y plane defined from said maximum x-y-z vector and minimum x-y-z vector together with virtual z axis defined from 45 degree rotation about said maximum virtual x-y-z vector.

15. A system of claim 14, further comprising a display that shows the location of said sensor coil in said subject relative to the array of triplet drive coils.

16. A system of claim 15, wherein the display displays said disposition of said sensor coil in said subject indicating height, width, and/or depth in said subject relative to said triplet drive coil sets.

17. A system of claim 15, wherein said display displays the sensor coil angle graphically for the user of said system, wherein said sensor coil angle is measured as the angle of maximum demodulated sensor coil response from a sweep through x, y, and z virtual axes.

18. A system of claim 15, wherein said display displays the sensor coil angle graphically for the user of said system, wherein said sensor coil angle is the angle perpendicular to the angle of minimum demodulated sensor coil response from a sweep through x, y, and z virtual axes.

19. A system of claim 1, further comprising (i) an x-axis tilt meter and y-axis tilt meter which uses gravity to measure the x-axis and y-axis tilt from true vertical; and (ii) a computer to calculate and display said disposition of said tip as height, width, and depth of the sensor coil corrected for the tilt of said array of triplet drive coil sets.

20. A system of claim 5, wherein said triplet drive coil array and said sensor coil are independently connected to said display via wireless interfaces.

21. A system according to claim 1, further comprising a catheter disposed in physical association with said sensor coil.

22. A system according to claim 21 wherein the sensor coil is disposed in physical association with one of the distal portion, the end or the tip of said catheter.

23. A system according to claim 1, further comprising one or more of a guide wire and a stylet disposed in physical association with said sensor coil.

24. A system according to claim 23, wherein the sensor coil is disposed in physical association with one of the distal portion, the end or the tip of said guide wire or stylet.

25. A system according to claim 23, wherein a sterile locking fitting is used to lock said guide wire or stylet with the said sensor coil into a position common with one of the distal portion, the end or the tip of a catheter.

26. A system of claim 1, further comprising an electrocardiogram (ECG) operably associated with said triplet drive coil array wherein the one or more ECG reference leads are placed on said subject and the ECG signal lead is provided by a conductive core wire supporting said sensor coil herewith a display to show said subject's ECG signal over time.

27. A system of claim 26, wherein said display further displays the subject's P-wave changes over time in combination with said location of said sensor coil in relationship to said subject's heart.

28. A system according to claim 26, further comprising one or more of a catheter, a guide wire and a stylet with said sensor coil being disposed in physical association therewith, and further comprising an integrated conductive ECG lead associated with the sensor coil, the conductive ECG lead providing an electrical ECG signal.

29. A system for one or both of two- or three-dimensional location of the disposition of a sensor coil in a subject comprising:
- an array of electromagnetic drive coil sets, each set having an arrangement of three-dimensionally oriented drive coils;
- a sensor coil being electromagnetically communicative with the array of electromagnetic drive coil sets; and,
- a system controller communicative with and adapted to energize one or more of the electromagnetic coils in the array of electromagnetic drive coil sets, the energizing of the one or more of the electromagnetic coils including one or more of energizing the coils singly, or in pairs or in triplets of coils while measuring the response of the sensor coil;
- whereby the system uses the measurements of the responses of the sensor coil to calculate the location and orientation of the sensor coil relative to said drive coil sets.

30. A method for locating a medical device in a subject, comprising:
a. providing a system of claim 1;
b. inserting and positioning said medical device tip associated with a functional and sterile medical device into said subject;
c. recording or monitoring the output of said display to locate said medical device tip in said subject.

31. A method of claim 1, wherein said method further comprises the use of at least one selected from an x-ray machine, an computer assisted tomography (CAT) machine, a positron emission tomography (PET) machine, an endoscope, or an imaging device or composition.

32. A method for generating virtual electromagnetic triplet drive axes for generating data corresponding to the location coordinates for said sensor coil, comprising:
a. electronically providing triplets of drive current values generated from at least three said discrete drive coils of said triplet drive coils in detectable proximity to said sensor coil at regular time intervals to provide one or more paired magnetic drive coil vector values generated at angles from 0 to 90 degrees without and from −90 to 0 degrees with phase inversion;
b. electronically providing angle values of maximum and minimum sensor coil responses generated from said triplet drive coils within a plane using paired coil programmable current drive sweeping a range from 0 to 90 degrees without and from −90 to 0 degrees with phase inversion;
c. electronically computing at least one set of optimal virtual drive x and y axes as values corresponding to plus and minus 45 degrees from said maximum or minimum sensor coil responses;
d. electronically computing an optimal virtual drive z axis orthogonal to the plane of said optimal virtual drive x and y axes to provide at least one optimal virtual triplet drive vector and at least one of said triplet drive coils.

33. A method according to 32, wherein
a. said triplets of drive current values selected at regular time intervals are provided as (i) paired magnetic drive coil vector values at angles from 0 to 90 degrees in an x-y plane together with 0 to 90 degrees from said x-y plane to the corresponding z-axis; and (ii) as phase inversions of one or two paired magnetic drive coil vector values at angles from −90 to 0 degrees in an x-y plane together with from −90 to 0 degrees from said x-y plane to the corresponding z-axis;
b. said angle values of maximum sensor coil responses within a plane for both 0 to 90 and −90 to 0 degrees are fixed and used for at least two x and y virtual axes in a virtual plane and said values of maximum sensor coil response are determined for the corresponding virtual z axis to provide at least one maximum virtual x-y-z vector for at least one of said corresponding triplet drive coils;
c. said angle values of minimum sensor coil responses within a plane for both 0 to 90 and −90 to 0 degrees are fixed and used for at least two x and y virtual axes in a virtual plane and said values of minimum sensor coil response are determined for the corresponding virtual z axis to provide at least one minimum virtual x-y-z vector for at least one of said corresponding triplet drive coils;
d. said at least one optimal virtual EM triplet drive axes for at least one of said triplet drive coils are generated using virtual drive x axis and y axis 45 degree rotation from said maximum virtual x-y-z vector and minimum virtual x-y-z vector with the virtual drive z axis as orthogonal to said virtual drive x and y axis and rotated 45 degrees about said maximum virtual x-y-z vector.

* * * * *